(12) United States Patent
Shibuya et al.

(10) Patent No.: US 11,094,885 B2
(45) Date of Patent: Aug. 17, 2021

(54) FULLERENE DERIVATIVES AND PHOTOELECTRIC DEVICE AND IMAGE SENSOR

(71) Applicant: Samsung Electronics Co., Ltd., Suwon-si (KR)

(72) Inventors: Hiromasa Shibuya, Seongnam-si (KR); Norihito Ishii, Suwon-si (KR); Yeong Suk Choi, Suwon-si (KR); Yutaka Matsuo, Tokyo (JP)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 189 days.

(21) Appl. No.: 16/201,345

(22) Filed: Nov. 27, 2018

(65) Prior Publication Data

US 2019/0173015 A1    Jun. 6, 2019

(30) Foreign Application Priority Data

Dec. 4, 2017 (KR) .......................... 10-2017-0165360

(51) Int. Cl.
*H01L 51/00* (2006.01)
*C07D 307/93* (2006.01)
(Continued)

(52) U.S. Cl.
CPC ........ *H01L 51/0047* (2013.01); *C07D 307/77* (2013.01); *C07D 307/93* (2013.01);
(Continued)

(58) Field of Classification Search
CPC ............. H01L 51/0046; H01L 51/0047; H01L 51/4253
See application file for complete search history.

(56) References Cited

U.S. PATENT DOCUMENTS 6,300,612 B1   10/2001   Yu
7,129,466 B2   10/2006   Iwasaki
(Continued)

FOREIGN PATENT DOCUMENTS

EP    3070756 A1       9/2016
JP    2012015390 A  *  1/2012
KR    20170047370 A    5/2017

OTHER PUBLICATIONS

English machine translation of Hattori et al. (JP 2012-015390 A) provided by the EPO website. (Year: 2020).*

(Continued)

*Primary Examiner* — Daniel P Malley, Jr.
(74) *Attorney, Agent, or Firm* — Harness, Dickey & Pierce, P.L.C.

(57) ABSTRACT

Disclosed are a fullerene derivative including a substituent represented by Chemical Formula 1, and a photoelectric device, an image sensor, and an electronic device including the fullerene derivative.

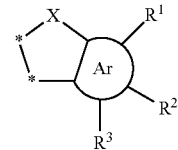

[Chemical Formula 1]

In Chemical Formula 1, X, Ar, and $R^1$ to $R^3$ are the same as defined in the detailed description.

18 Claims, 7 Drawing Sheets

(51) Int. Cl.
  *C09K 11/06* (2006.01)
  *C07D 307/77* (2006.01)
  *H01L 27/30* (2006.01)
  *H01L 51/42* (2006.01)
(52) U.S. Cl.
  CPC ............ *C09K 11/06* (2013.01); *H01L 27/307* (2013.01); *H01L 51/4253* (2013.01); *C09K 2211/1011* (2013.01); *C09K 2211/1014* (2013.01); *C09K 2211/1096* (2013.01); *H01L 51/424* (2013.01)

(56) References Cited

U.S. PATENT DOCUMENTS

| | | | |
|---|---|---|---|
| 7,973,307 | B2 | 7/2011 | Rand et al. |
| 8,035,708 | B2 | 10/2011 | Takizawa et al. |
| 8,426,727 | B2 | 4/2013 | Pfeiffer et al. |
| 9,039,935 | B2 | 5/2015 | Nakamura et al. |
| 9,231,214 | B2 | 1/2016 | Tolbert et al. |
| 10,374,162 | B2 * | 8/2019 | Blouin ................ H01L 51/0036 |
| 2007/0012955 | A1 | 1/2007 | Ihama |
| 2012/0313088 | A1 | 12/2012 | Yofu et al. |
| 2017/0069690 | A1 | 3/2017 | Sakurai et al. |
| 2017/0092686 | A1 | 3/2017 | Kasai |
| 2017/0092868 | A1 | 3/2017 | Yagi et al. |
| 2017/0294585 | A1 * | 10/2017 | Morse ................ H01L 51/4253 |

OTHER PUBLICATIONS

STN structure search for U.S. Appl. No. 16/201,345. 2020 (Year: 2020).*
Extended European Search Report dated May 23, 2019, issued in corresponding European Patent Application No. 18208263.6.
S. Lu et al., 'Co-Catalyzed Radical Cycloaddition of [60]Fullerene with Active Dibromides: Selective Synthesis of Carbocycle-Fosed Fullerene Monoadducts'. *Organic Letters*. vol. 15, No. 15, Jul. 2013, pp. 4030-4033.
M. Saunders et al., 'Reaction of Cyclopropa[b]naphthalene with $^3$He@$C_{60}$' *Tetrahedron Letters*, vol. 35, No. 23, 1994, pp. 3869-3872.
Y.T. Su et al., 'Palladium-catalyzed heteroannulation of [60]fullerene with N-(2-arylethyl) sulfonamides via C—H bond activation' *Organic Chemistry Frontiers*, vol. 1, 2014, pp. 689-693.
T.X. Liu et al., 'Synthesis of [60]Fullerene-Fused Tetrahydronaphthalene and Indane Derivatives via a Pathway Switched by Aluminum Chloride' *Organic Letters*, vol. 13, No. 22, Sep. 2011, pp. 6130-6133.
Y.T. Su et al., 'Paliadium-catalysed heteroannulation of [60]fullerene with N-benzyl sulfonamides and subsequent functionalisation' *Chem. Commun.*, vol. 46, May 2012, pp. 8132-8134.

E. Beer et a., 'Funktionalisierung von Buckminsterfulleren $C_{60}$ durch [8 + 2]-Cycloaddition: spektroskopishe und Elektronentransfereigenschaften eines Tetrahydroazulenofullerens' *Angew. Chem.*, vol. 106, No. 10, 1994, pp. 1140-1142.
European Search Report dated Feb. 15, 2019 issued in corresponding European Application No. 18208263.6.
Yi-Tan Su et al., "$FeCl_3$-Mediated Cyclization of [60]Fullerene with N-Benzhydryl Sulfonamides under High-Speed Vibration Milling Conditions"; Organic Letters, vol. 15, No. 13, Jun. 17, 2013, pp. 3408-3411.
Adams D. Darwish et al.; "Electrophillic substitution of $C_{60}F_{18}$ into phenols: HF elimination between OH and 1,3,-shifted fluorine giving benzofurano[2'3'10,26]hexadecafluoro[60]fullerene and derivatives". Organic & Biomolecular Chemistry, vol. 1, No. 1, Apr. 8, 2003, pp. 1764-1768.
Yutaka Matsuo et al.; "Fullerene cation-mediated demethylation/ cyclization to give 5- and 7-membered cyclo[60] fullerene derivatives"; Journal of Materials Chemistry A, vol. 5, No. 6, Dec. 20, 2016, pp. 2774-2783.
Fei Li et al., "Palladium-catalyzed synthesis of [60 ] fullerene-fused benzofurans via heteroannulation of phenols".; Chemical Communications, vol. 53, No. 11, Jan. 13, 2017, pp. 1852-1855.
Masakazu Nambo et al., "Aziridinofullerene: A Versatile Platform for Functionalized Fullerenes", Journal of the American Chemical Society, vol. 133, No. 8, Feb. 8, 2011, pp. 2402-2405.
Y. Numata et al, "Subsituent Effect on the Reduction Potentials of Heterocyclic-fused[60]Fullerene Derivatives". ECS Transactions, Jan. 1, 2009, pp. 33-43.
Bo Zhu et al., "Synthesis of [60]Fulleroindolines: Palladium-Catalyzed Heteroannulations of [60]Fullerene with o-iodoanilines", Journal of Organic Chemistry, vol. 74, No. 11, Apr. 30, 2009, pp. 4426-4428.
Y. An et al., "Synthesis of α-Amino Acid Derivatives of $C_{60}$ from 1,9-(4-Hydroxycyclohexano)-buckminsterfullerene" J. Org. Chem. 58, 4799-4801 (1993).
F. Li et al., "Palladium-catalyzed synthesis of [60]fullerene-fused benzofurans via heteroannulation of phenols" Chemical Communications, 53, 11, 1852-1855.
M. Nambo et al., "Aziridinofullerene: A versatile Platform for Functionalized Fullerenes" J. Am. Chem. Soc. 2011, 133, 2402-2405.
Y. Zhang et al., "A Scalable Synthesis of Methano[60]fullerene and Congeners by the Oxidative Cyclopropanation Reaction of Silylmethylfullerene" J. Am. Chem. Soc. 133, 8086-8089 (2011).
Y. Matsuo et al., "Fullerene Cation-mediated Demethylation/ Cyclization to 5- and 7-Membered cyclo[60]fullerene Derivatives" Journal of Materials Chemistry A, 5, 6 2774-2783.
A. Darwish et al., "Electrophilic substitution of $C_{60}F_{18}$ into phenols: HF elimination between OH and a 1,3-shifted fluorine giving benzofurano[2',3':10,26]hexadecafluoro[60]fullerene and derivatives" Org. Biomol. Chem., 2003, 1, 1764-1768.

* cited by examiner

FULLERENE DERIVATIVES AND PHOTOELECTRIC DEVICE AND IMAGE SENSOR

CROSS-REFERENCE TO RELATED APPLICATION

This application claims priority to and the benefit of Korean Patent Application No. 10-2017-0165360 filed in the Korean Intellectual Property Office on Dec. 4, 2017, the entire contents of which are incorporated herein by reference.

BACKGROUND

(a) Field

Fullerene derivatives, photoelectric devices, and image sensors are disclosed.

(b) Description of Related Art

Fullerene is a molecule having a closed-cage structure composed of carbons and used in various fields due to its stable structure and satisfactory electric characteristics. Recently, various fullerene derivatives have been developed by combining the fullerene with a substituent.

A photoelectric device may convert light into an electrical signal using photoelectric effects, it may include a photodiode, a phototransistor, and the like, and it may be applied to an electronic device such as an image sensor. The photoelectric device may include fullerene having high light absorption characteristics and satisfactory electric characteristics or a derivative thereof.

SUMMARY

An embodiment provides a novel fullerene derivative applicable to a photoelectric device.

Another embodiment provides a photoelectric device including the fullerene derivative.

Yet another embodiment provides an image sensor including the photoelectric device.

According to an embodiment, a fullerene derivative including a substituent represented by Chemical Formula 1 is provided.

[Chemical Formula 1]

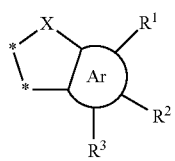

In Chemical Formula 1, Ar may be a C6 to C30 aromatic ring.

X may be one of O, S, Se, Te, SO, $SO_2$, $NR^a$, $CR^bR^c$, $SiR^dR^e$, or $GeR^fR^g$, $R^1$ to $R^3$ and $R^a$ to $R^g$ may independently be one of hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C6 to C30 aryl group, a substituted or unsubstituted C3 to C30 heterocyclic group, a halogen, a cyano group, or a combination thereof, and

* may be a linking point with a fullerene core.

provided that when Ar is a benzene ring, Chemical Formula 1 is represented by Chemical Formula 2,

[Chemical Formula 2]

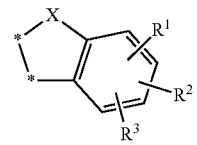

wherein, in Chemical Formula 2,

X and $R^1$ to $R^3$ are the same as defined in Chemical Formula 1, and at least two of $R^1$ to $R^3$ may independently be a substituted or unsubstituted C3 to C20 branched alkyl group.

In some example embodiments, the fullerene derivative may be a vacuum-depositable compound by sublimation.

In some example embodiments, the fullerene derivative may exhibit 10% weight loss relative to an initial weight occurs at a temperature of less than or equal to about 450° C., and the fullerene derivative may exhibit 50% weight loss relative to the initial weight occurs at a temperature of less than or equal to about 500° C. at a thermogravimetric analysis at 1 Pa or less.

In some example embodiments, the fullerene derivative may have a LUMO energy level of about 3.7 eV to about 5.0 eV and the fullerene derivative may have a HOMO energy level of about 5.8 eV to about 7.0 eV.

In some example embodiments, the Ar may be a benzene ring or a fused ring.

In some example embodiments, the Ar may be one of a benzene ring, a naphthalene ring, an anthracene ring, a phenanthrene ring, a pyrene ring, or a triphenylene ring.

In some example embodiments, the fullerene core may be one of C60, C70, C74, C76, or C78.

In some example embodiments, at least two of R1 to R3 of Chemical Formula 2 may independently be one of an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

In some example embodiments, the substituent represented by Chemical Formula 2 may be represented by one of Chemical Formulae 3 to 8.

[Chemical Formula 3]

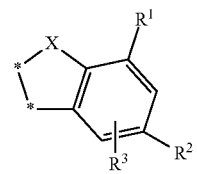

[Chemical Formula 4]

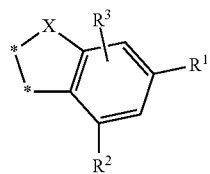

[Chemical Formula 5]

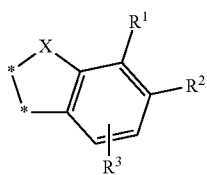

[Chemical Formula 6]

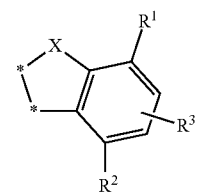

[Chemical Formula 7]

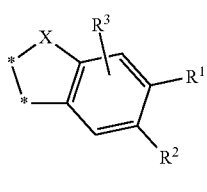

[Chemical Formula 8]

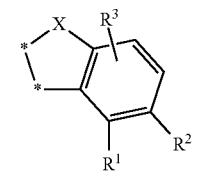

In Chemical Formulae 3 to 8, $R^1$ and $R^2$ may independently be a substituted or unsubstituted C3 to C20 branched alkyl group.

In some example embodiments, the substituent represented by Chemical Formula 1 may be represented by one of Chemical Formulae 1A to 1F.

[Chemical Formula 1A]

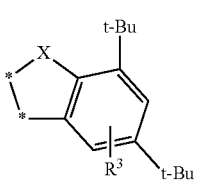

[Chemical Formula 1B]

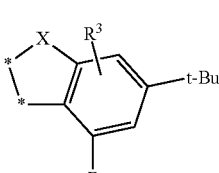

[Chemical Formula 1C]

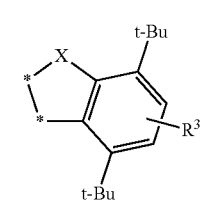

[Chemical Formula 1D]

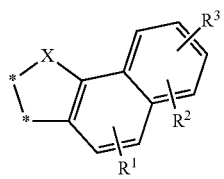

[Chemical Formula 1E]

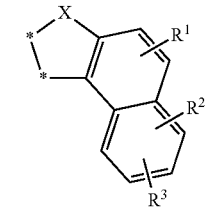

[Chemical Formula 1F]

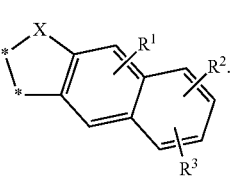

According to another embodiment, a thin film including the fullerene derivative is provided.

In some example embodiments, an extinction coefficient at a wavelength of 450 nm of the thin film may be smaller than an extinction coefficient at a wavelength of 450 nm of a thin film including unsubstituted C60 fullerene.

In some example embodiments, the extinction coefficient at a wavelength of 450 nm of the thin film may be less than or equal to about ½ of the extinction coefficient at a wavelength of 450 nm of a thin film including unsubstituted C60 fullerene.

According to yet another embodiment, a photoelectric device includes a first electrode and a second electrode facing each other and an organic layer between the first electrode and the second electrode. The organic layer may include a fullerene derivative including a substituent represented by Chemical Formula 1.

In some example embodiments, the organic layer may include an active layer, the active layer may include a p-type semiconductor and an n-type semiconductor that form a pn junction, and the n-type semiconductor may include the fullerene derivative.

According to another embodiment, an image sensor includes the photoelectric device.

According to yet another embodiment, an electronic device includes the image sensor.

According to still another embodiment, an electronic device includes the photoelectric device.

The fullerene derivative satisfying desired optical characteristics and electric characteristics is provided and characteristics of a photoelectric device and an electronic device including the same may be improved.

DETAILED DESCRIPTION

Figure 1:
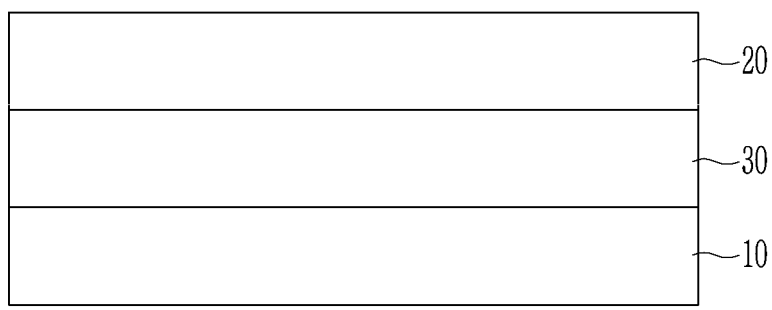
FIG. 1 is a cross-sectional view showing a photoelectric device according to an embodiment.

Hereinafter, example embodiments of the present disclosure will be described in detail so that a person skilled in the art would understand the same. This disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Hereinafter, "combination" refers to a mixture of two or more and a stack structure of two or more.

As used herein, when a definition is not otherwise provided, "substituted" refers to replacement of hydrogen of a compound or a group by a substituent selected from a halogen atom, a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C20 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when a definition is not otherwise provided, "hetero" refers to one including one to three heteroatoms selected from N, O, S, P, and Si, and remaining carbons in one functional group.

As used herein, when a definition is not otherwise provided, "aryl group" refers to a group including at least one aromatic hydrocarbon moiety, for example all the elements of the aromatic hydrocarbon moiety having p-orbitals which form conjugation such as a phenyl group or a naphthyl group; two or more aromatic hydrocarbon moieties linked by a sigma bond such as a biphenyl group, a terphenyl group, or a quarterphenyl group; and two or more aromatic hydrocarbon moieties fused directly or indirectly to provide a non-aromatic fused ring such as a fluorenyl group.

As used herein, when a definition is not otherwise provided, "heterocyclic group" is a generic concept of a heteroaryl group, and may include at least one heteroatom instead of carbon (C) in a ring such as an aryl group, a cycloalkyl group, a fused ring thereof, or a combination thereof wherein the heteroatom may be for example N, O, S, P, and/or Si, but is not limited thereto. When the heterocyclic group is a fused ring, at least one heteroatom may be included in an entire ring or each ring of the heterocyclic group.

As used herein, when a definition is not otherwise provided, "heteroaryl group" refers to an aryl group including at least one heteroatom, wherein the heteroatom may be for example N, O, S, P, and/or Si, but is not limited thereto. At least two heteroaryl groups may be linked directly through a sigma bond or at least two heterocyclic groups may be fused with each other. When the heteroaryl group is a fused ring, each ring may include one to three heteroatoms.

Hereinafter, a fullerene derivative according to an embodiment is described.

A fullerene derivative according to an embodiment comprises a substituent represented by Chemical Formula 1.

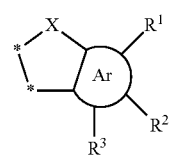

[Chemical Formula 1]

In Chemical Formula 1,

X is O, S, Se, Te, SO, $SO_2$, $NR^a$, $CR^bR^c$, $SiR^dR^e$, or $GeR^fR^g$,

Ar is a C6 to C30 aromatic ring, $R^1$ to $R^3$ and $R^a$ to $R^g$ are independently hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C6 to C30 aryl group, a substituted or unsubstituted C3 to C30 heterocyclic group, a halogen, a cyano group, or a combination thereof, and

* is a linking point with a fullerene core, provided that when Ar is a benzene ring, Chemical Formula 1 is represented by Chemical Formula 2,

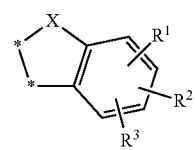

[Chemical Formula 2]

wherein, in Chemical Formula 2,

X, and $R^1$ to $R^3$ are the same as defined in Chemical Formula 1, and at least two of $R^1$ to $R^3$ are independently a substituted or unsubstituted C3 to C20 branched alkyl group.

In Chemical Formulae 1 and 2, $R^1$ to $R^3$ may be a substituent of Ar and the number of $R^3$ may be one or two or more.

The fullerene derivative has a structure substituted with a fused ring of a pentagonal ring (five-membered ring) and an aromatic ring and thus may increase a steric hindrance and reduce a π-conjugation system compared with unsubstituted fullerene. Accordingly, the fullerene derivative may decrease aggregation during the deposition compared with the unsubstituted fullerene and thus improve film-formation characteristics and reduce deformation of optical characteristics which may be caused by the aggregation. Particularly, the fullerene derivative comprising a substituent represented by Chemical Formula 2 has a plurality of branched alkyl groups and thus may lower a sublimation temperature and accordingly, be vacuum-deposited through sublimation without decomposition of a compound.

The fullerene derivative may be vacuum-deposited, for example, vacuum-deposited through sublimation. The vacuum deposition through sublimation may be examined through a thermogravimetric analysis (TGA), and in the thermogravimetric analysis, a temperature where a 10% weight loss relative to an initial weight under a pressure of less than or equal to about 1 Pa occurs may be for example less than or equal to about 450° C., and a temperature where a 50% weight loss relative to the initial weight may be less than about 500° C.

For example, the fullerene derivative may have a 10 wt % weight loss relative to the initial weight at about 300° C. to about 450° C. and a 50 wt % weight loss relative the initial weight at a temperature of greater than or equal to about 380° C. and less than about 500° C. during the thermogravimetric analysis under a pressure of less than or equal to about 1 Pa. Within the ranges, the 10 wt % weight loss relative to the initial weight may occur for example at about 310° C. to about 445° C. and the 50 wt % weight loss relative to the initial weight may occur for example at about 420° C. to about 490° C., within the ranges, the 10 wt % weight loss relative to the initial weight may occur for example at about 310° C. to about 425° C. and the 50 wt % weight loss relative to the initial weight may occur for example at about 420° C. to about 470° C., and within the ranges, the 10 wt % weight loss relative to the initial weight may occur for example at about 310° C. to about 410° C. and the 50 wt % weight loss relative to the initial weight may occur for example at about 420° C. to about 460° C.

The fullerene derivative may have a LUMO energy level of about 3.7 eV to about 5.0 eV and a HOMO energy level of about 5.8 eV to about 7.0 eV, a LUMO energy level of about 3.8 eV to about 4.9 eV and a HOMO energy level of about 6.0 eV to about 6.9 eV, a LUMO energy level of about 3.8 eV to about 4.8 eV and a HOMO energy level of about 6.0 eV to about 6.7 eV, or a LUMO energy level of about 3.8 eV to about 4.5 eV and a HOMO energy level of about 6.0 eV to about 6.5 eV. The fullerene derivative may have for example an energy band gap of about 2.0 eV to about 2.3 eV. When the fullerene derivative has an energy level within the ranges, it may be used as an n-type semiconductor effectively.

For example, Ar may be a benzene ring or a fused ring.

For example, Ar may be a benzene ring, a naphthalene ring, an anthracene ring, a phenanthrene ring, a pyrene ring, or a triphenylene ring.

For example, Ar may be a benzene ring or a naphthalene ring.

For example, the fullerene core may be C60, C70, C74, C76, or C78.

For example, the fullerene core may be C60.

For example, the fullerene derivative having the fullerene core bonded with the substituent represented by Chemical Formula 1 may be represented by Chemical Formula A.

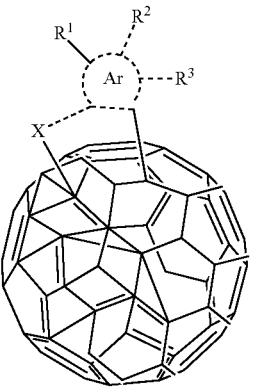

[Chemical Formula A]

In Chemical Formula A, X, Ar, and $R^1$ to $R^3$ are described above.

For example, Ar may be a benzene ring and at least one of $R^1$ to $R^3$ may be a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C6 to C30 aryl group, a substituted or unsubstituted C3 to C30 heterocyclic group, a halogen, a cyano group, or a combination thereof.

For example, Ar may be a benzene ring and at least two of $R^1$ to $R^3$ may be a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C6 to C30 aryl group, a substituted or unsubstituted C3 to C30 heterocyclic group, a halogen, a cyano group, or a combination thereof.

For example, Ar may be a benzene ring and at least one of $R^1$ to $R^3$ may be a substituted or unsubstituted C3 to C20 alkyl group, for example an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

For example, Ar may be a benzene ring and at least two of $R^1$ to $R^3$ may be a substituted or unsubstituted C3 to C20 alkyl group, for example an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

For example, Ar may be a fused ring, for example a naphthalene ring, an anthracene ring, a phenanthrene ring, a pyrene ring, or a triphenylene ring, and $R^1$ to $R^3$ may independently be hydrogen, deuterium, a substituted or unsubstituted C1 to C20 alkyl group, a substituted or unsubstituted C1 to C20 heteroalkyl group, a substituted or unsubstituted C2 to C20 alkenyl group, a substituted or unsubstituted C2 to C20 heteroalkenyl group, a substituted or unsubstituted C6 to C30 aryl group, a substituted or unsubstituted C3 to C30 heterocyclic group, a halogen, a cyano-containing group, or a combination thereof.

For example, at least two of $R^1$ to $R^3$ of Chemical Formula 2 may independently be a substituted or unsubstituted C3 to C20 alkyl group, for example a substituted or unsubstituted C3 to C20 branched alkyl group, for example an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

For example, the substituent represented by Chemical Formula 2 may be for example represented by one of Chemical Formulae 3 to 8.

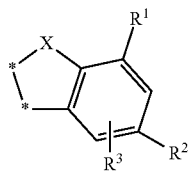

[Chemical Formula 3]

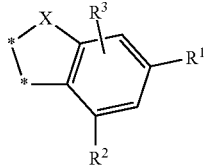

[Chemical Formula 4]

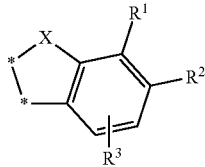

[Chemical Formula 5]

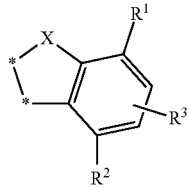

[Chemical Formula 6]

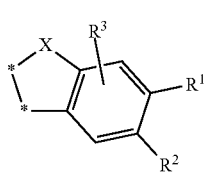

[Chemical Formula 7]

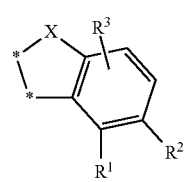

[Chemical Formula 8]

In Chemical Formulae 3 to 8, X and $R^3$ are as described above, and $R^1$ and $R^2$ are independently a substituted or unsubstituted C3 to C20 branched alkyl group.

For example, R1 and $R^2$ may independently be an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

For example, the substituent represented by Chemical Formula 1 may be represented by one of Chemical Formulae 1A to 1F, but is not limited thereto.

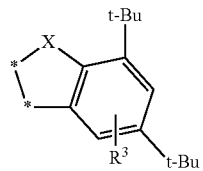

[Chemical Formula 1A]

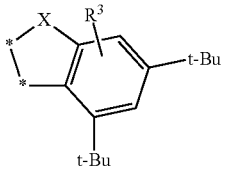

[Chemical Formula 1B]

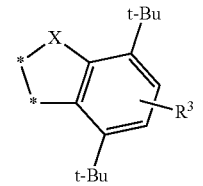

[Chemical Formula 1C]

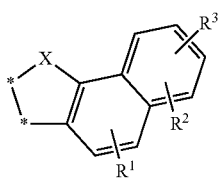

[Chemical Formula 1D]

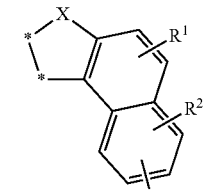

[Chemical Formula 1E]

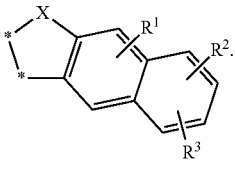

[Chemical Formula 1F]

In Chemical Formulae 1A to 1F, X and $R^1$ to $R^3$ are as described above.

The fullerene derivative may be for example one of compounds of Group 1, but is not limited thereto.

[Group 1]
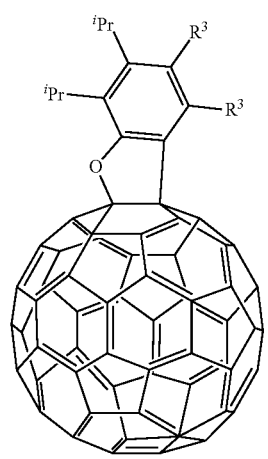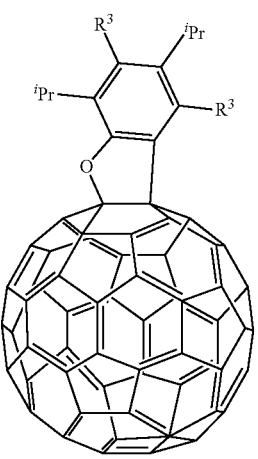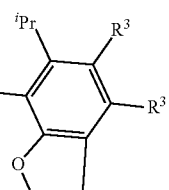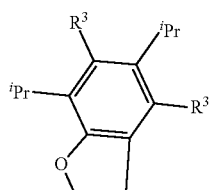
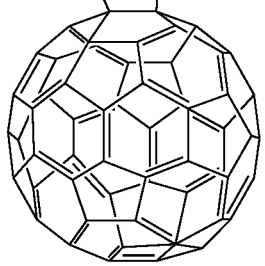
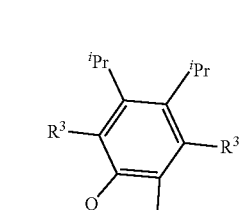
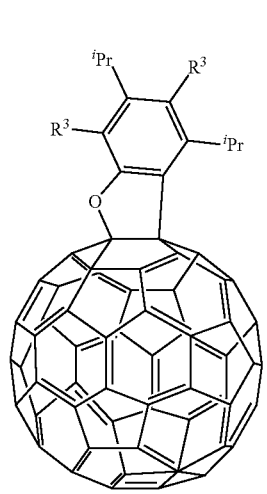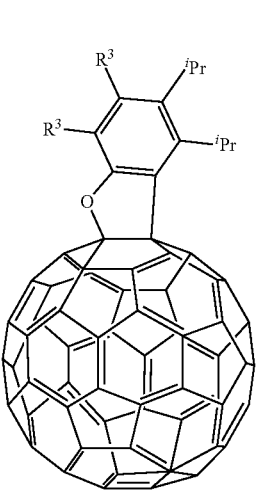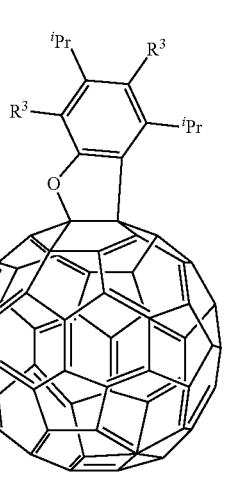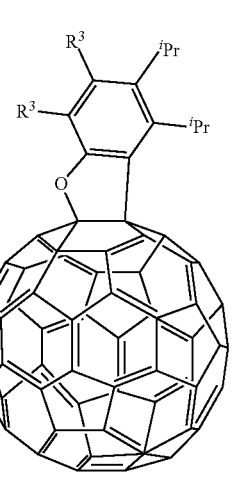

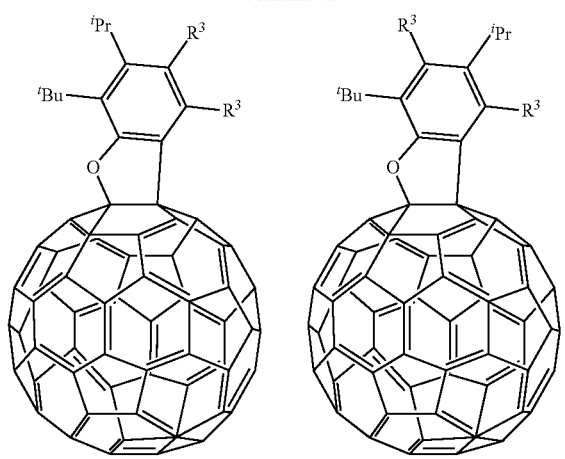
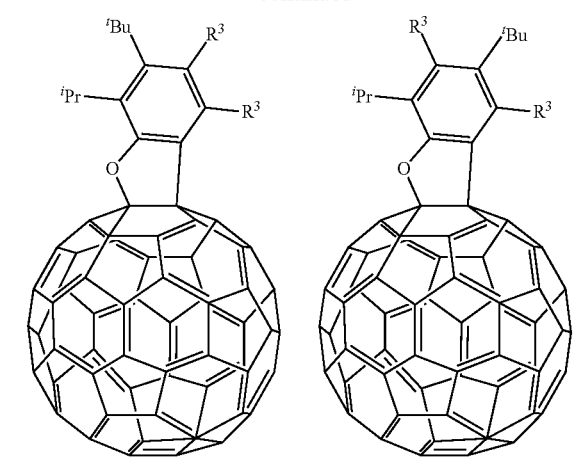
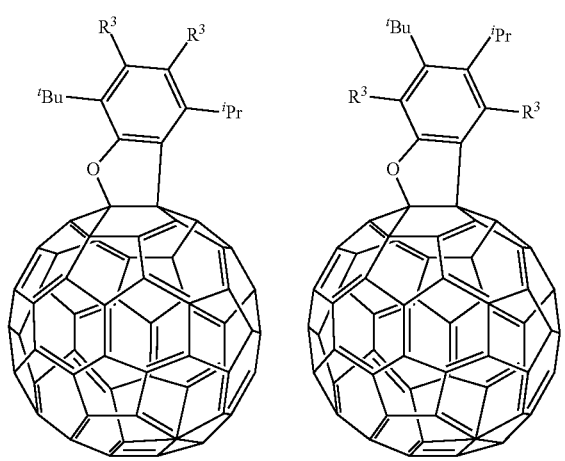
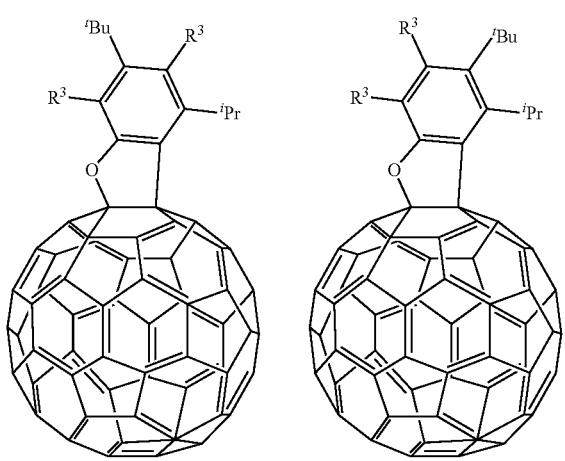

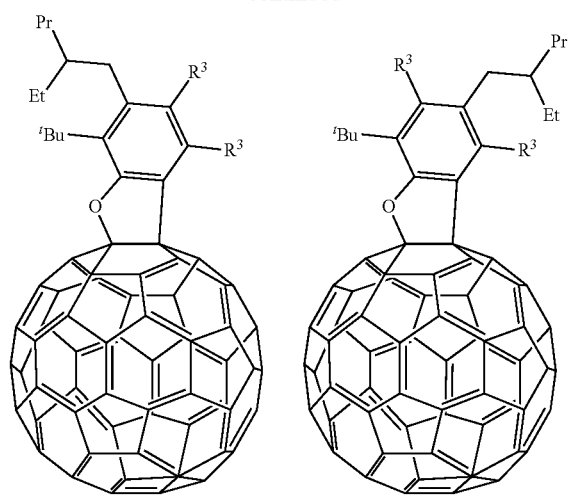
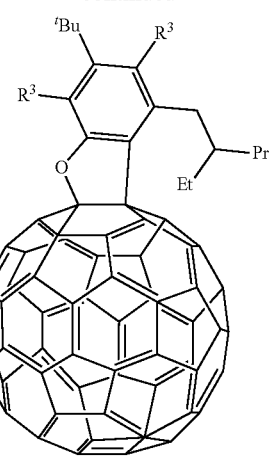
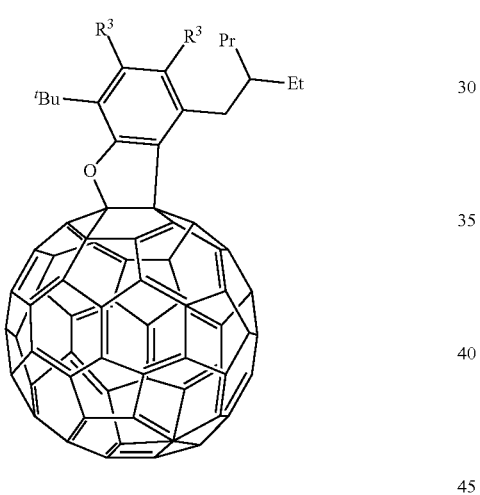
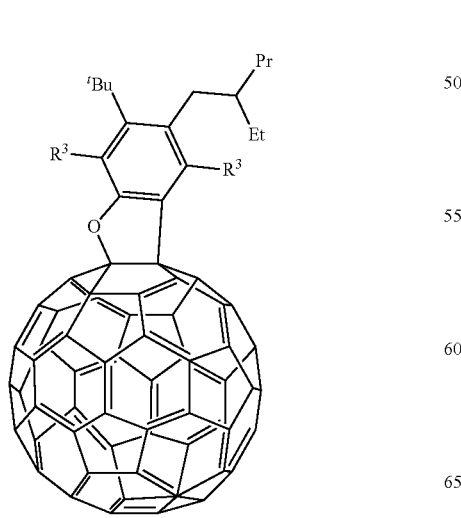
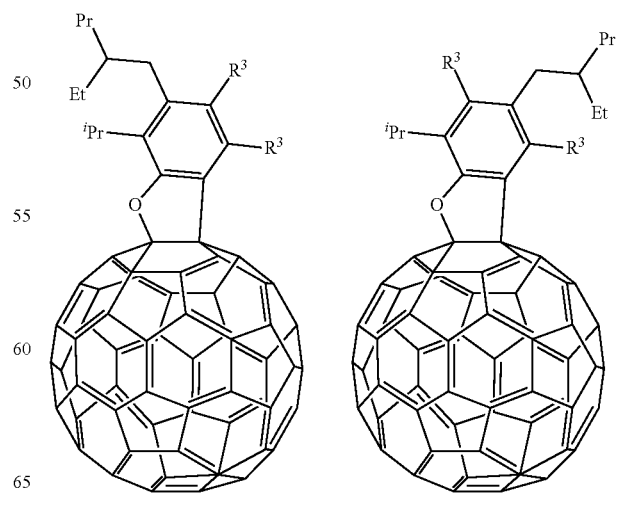

-continued
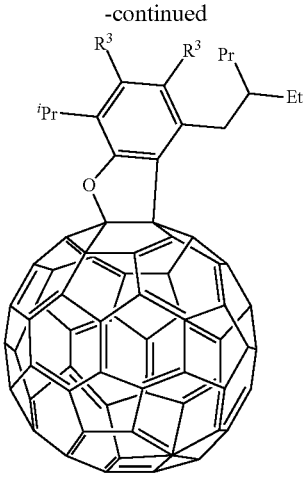
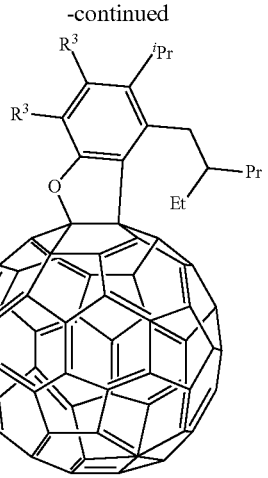
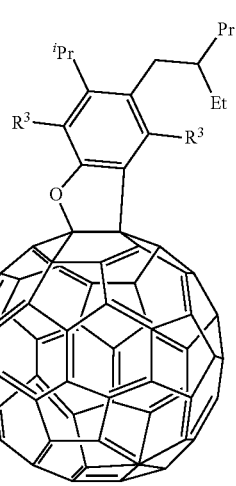
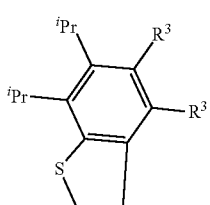 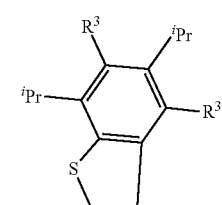
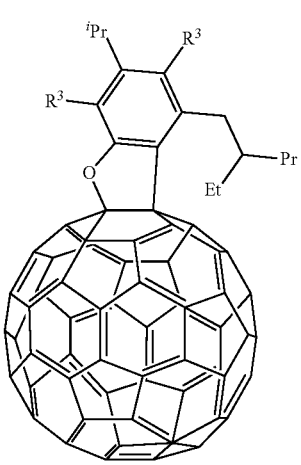
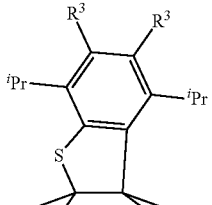 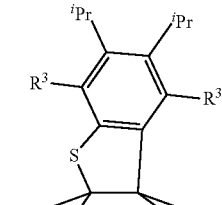

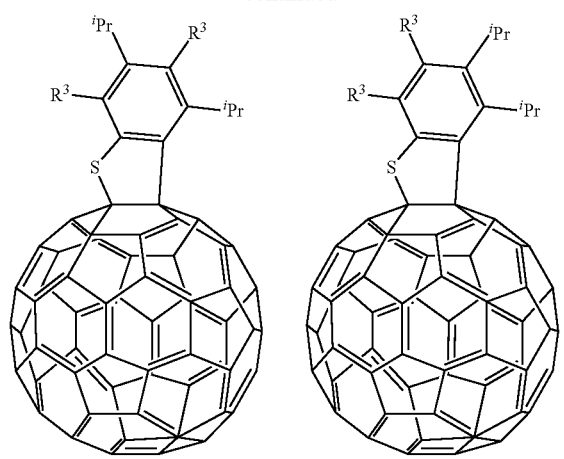
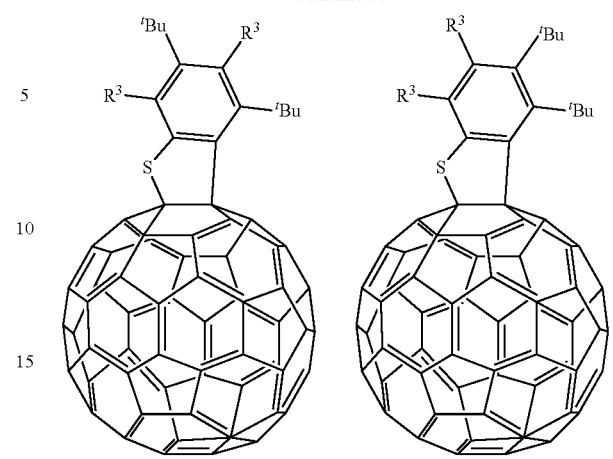
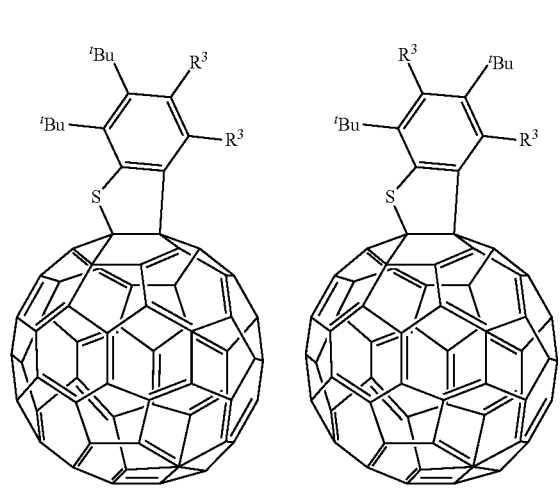
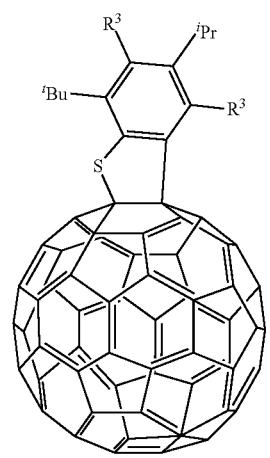
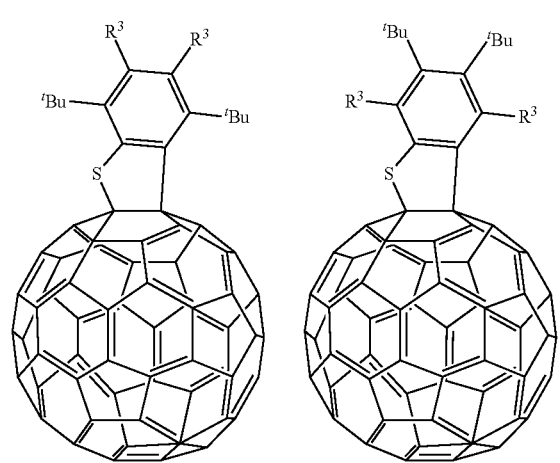
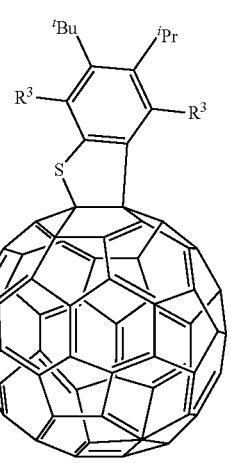

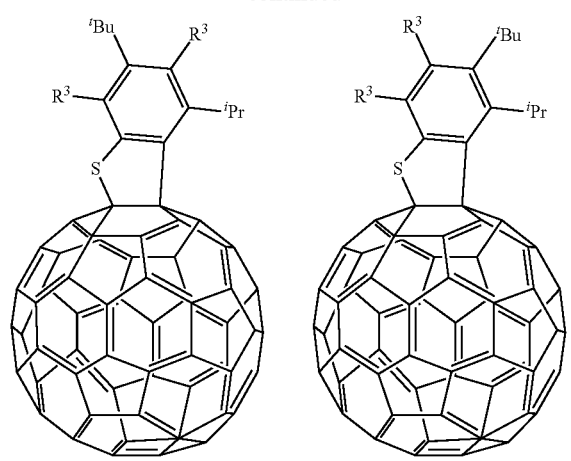
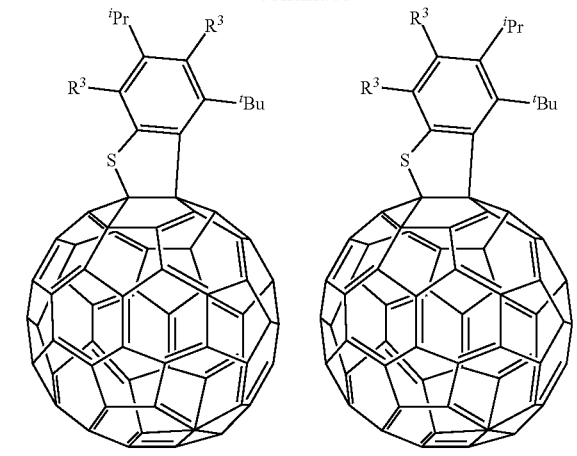
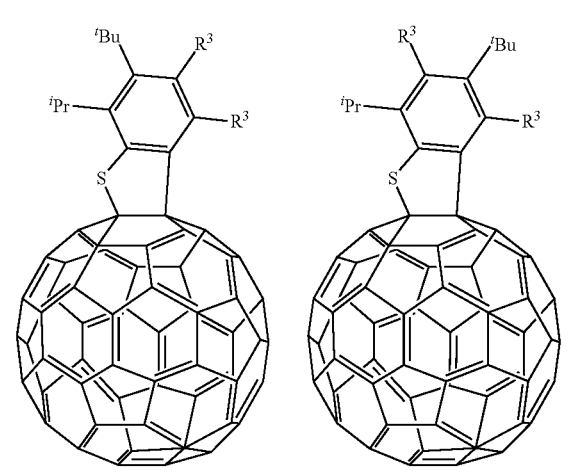
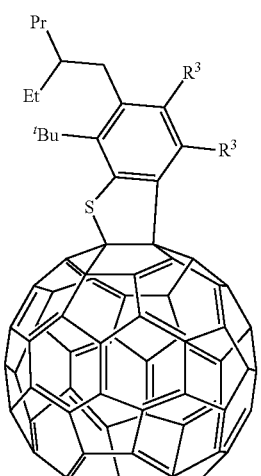
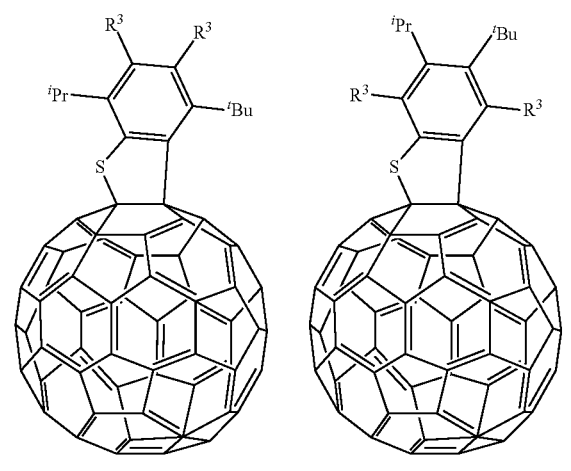
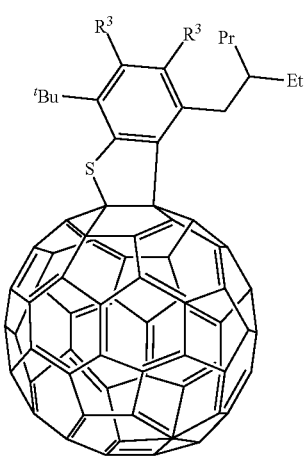

23
-continued
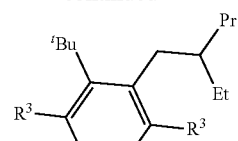
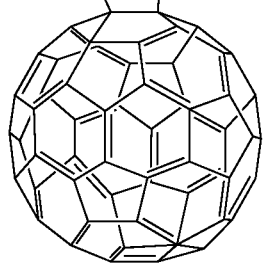
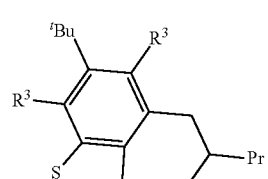
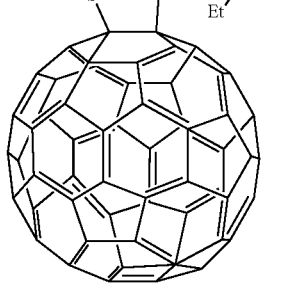
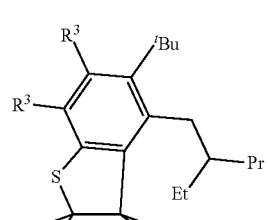
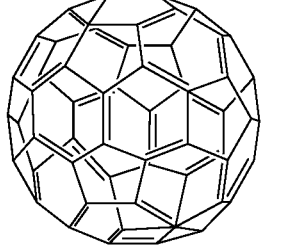
24
-continued
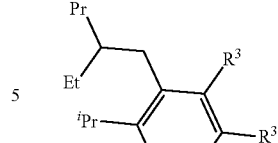
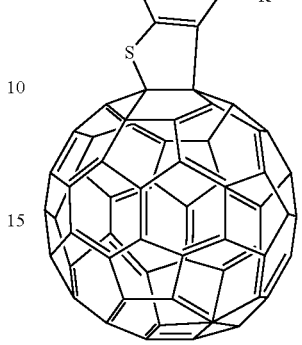
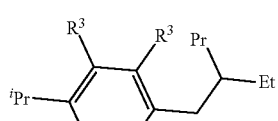
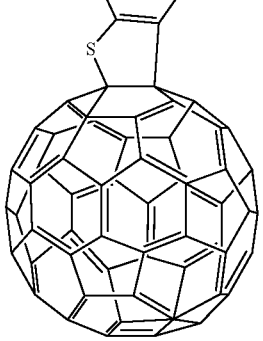
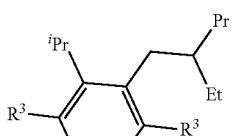
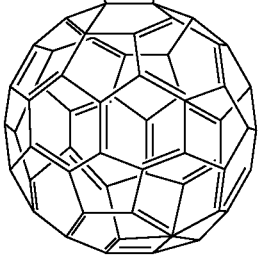

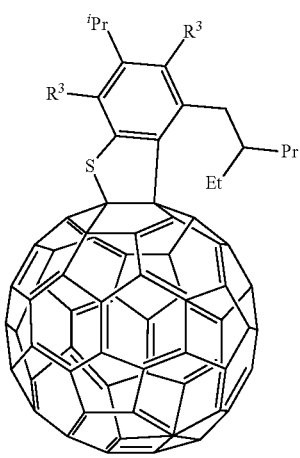
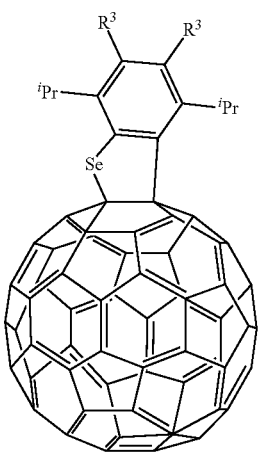
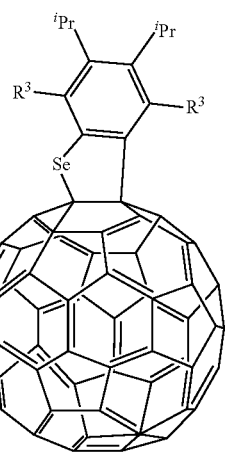
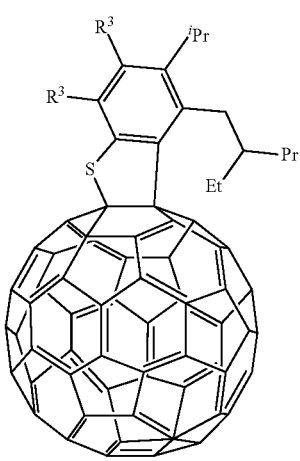
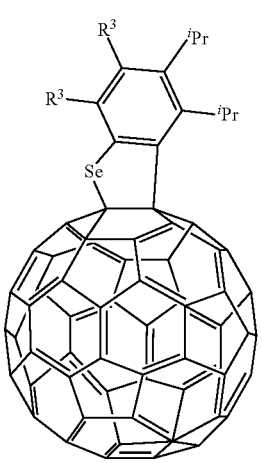
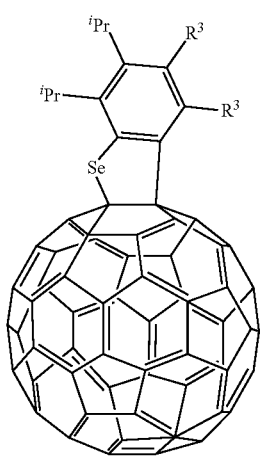
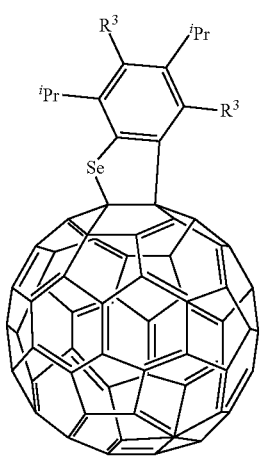
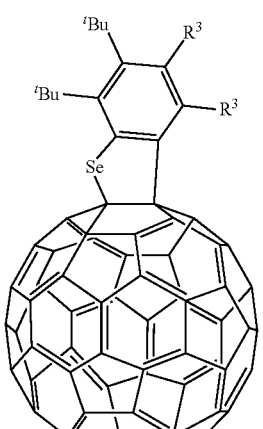
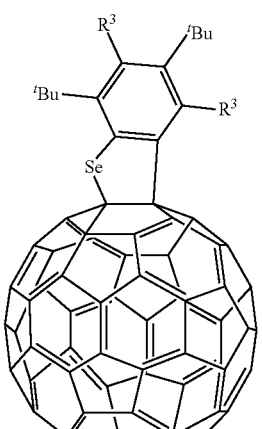

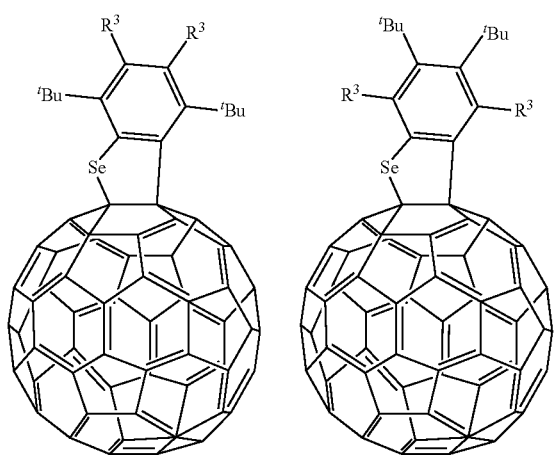
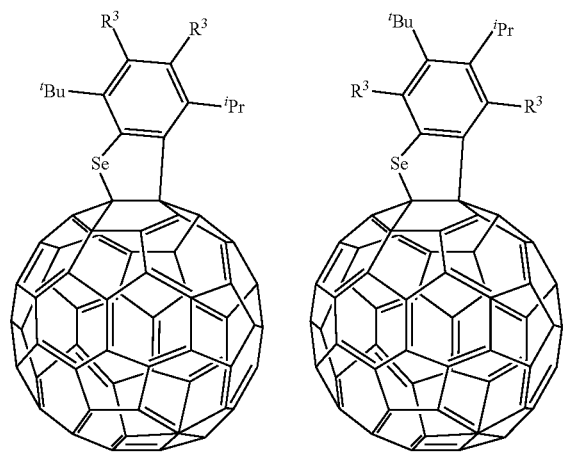
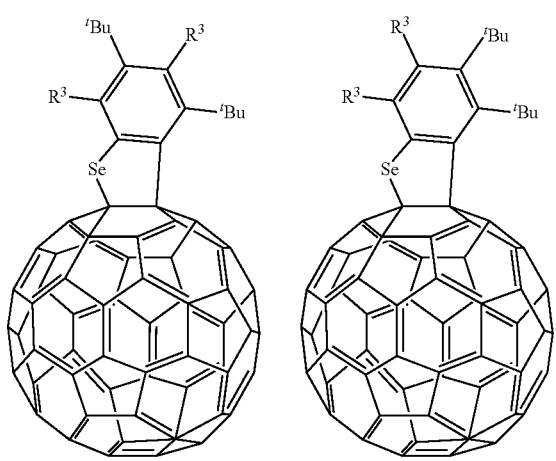
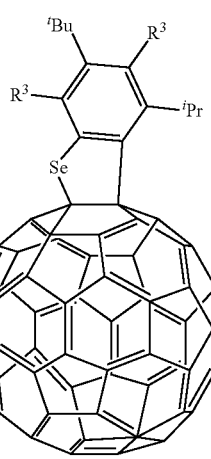
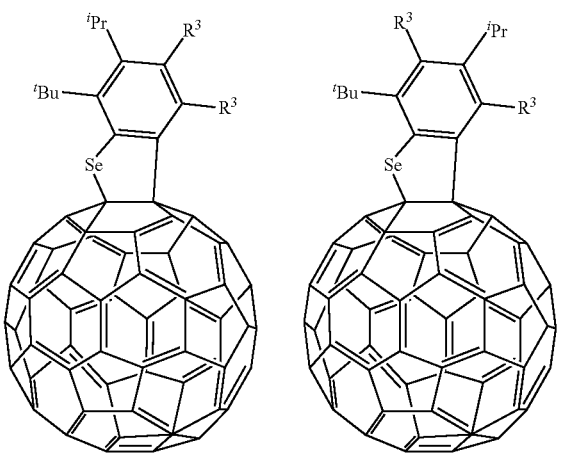
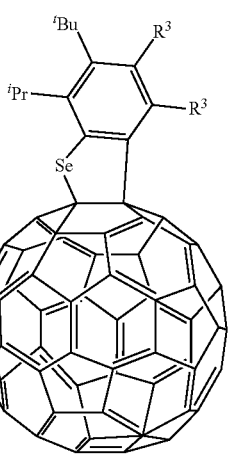

-continued
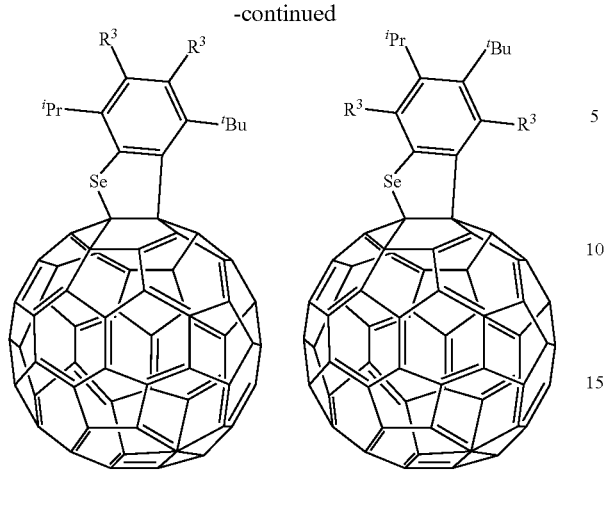
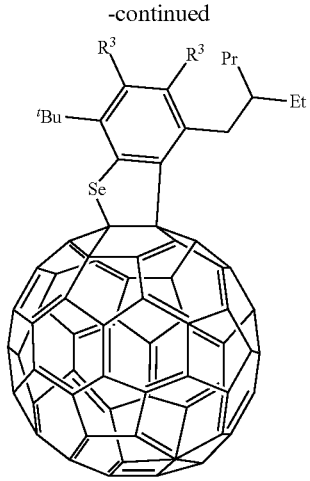
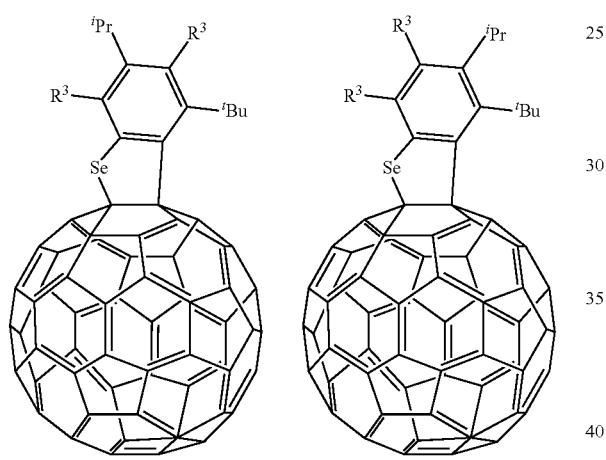
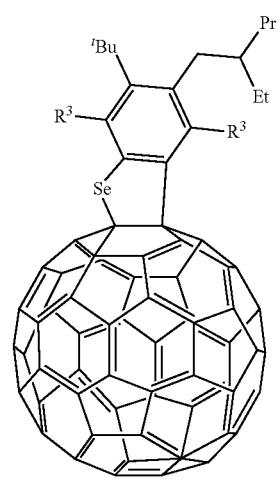
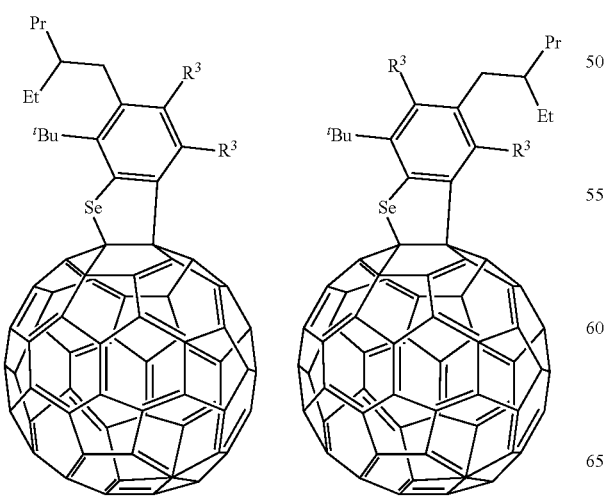
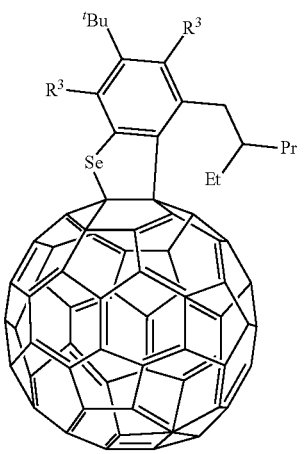

31
-continued
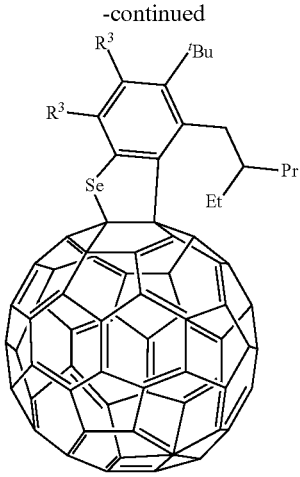
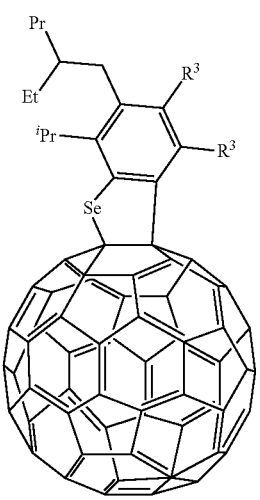 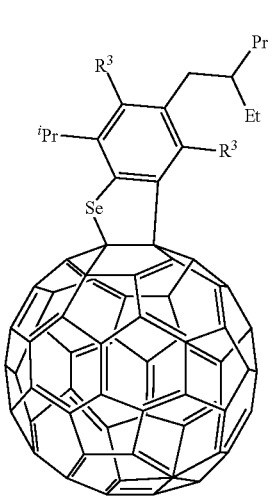
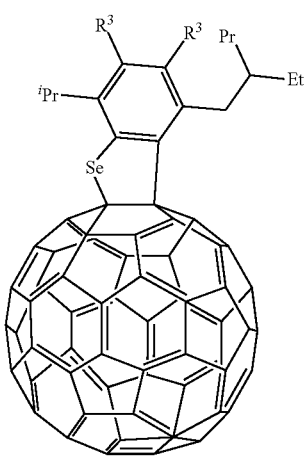
32
-continued
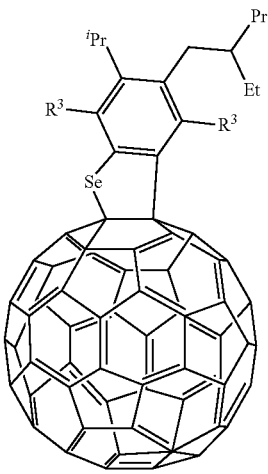
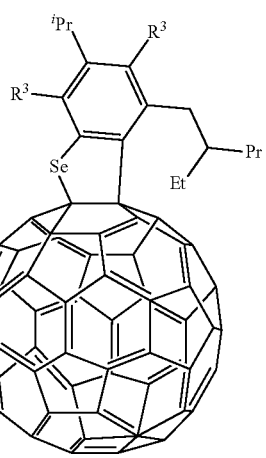
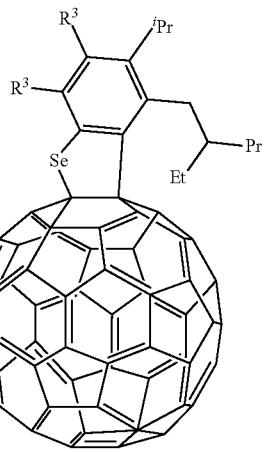

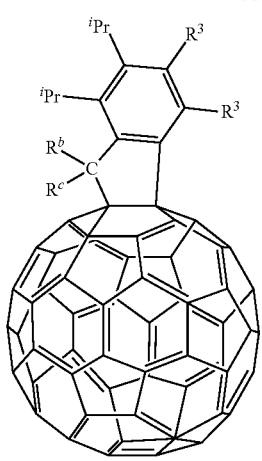
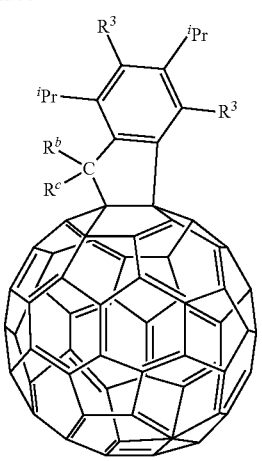
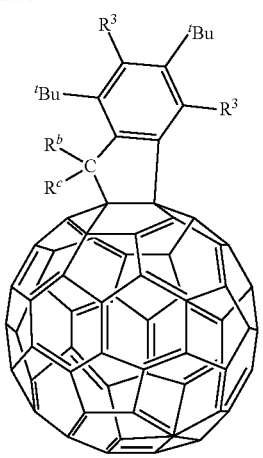
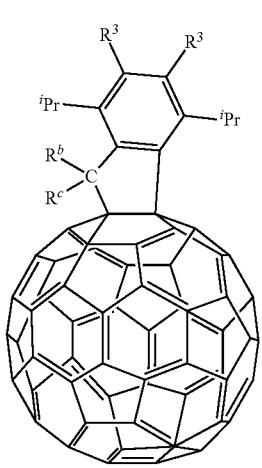
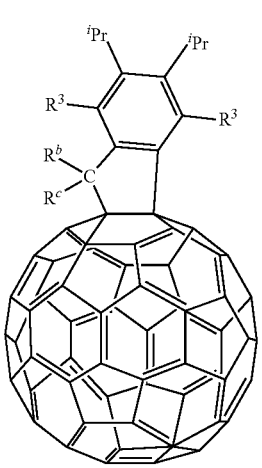
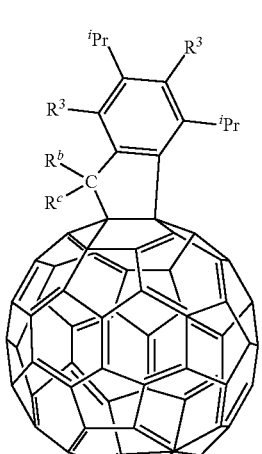
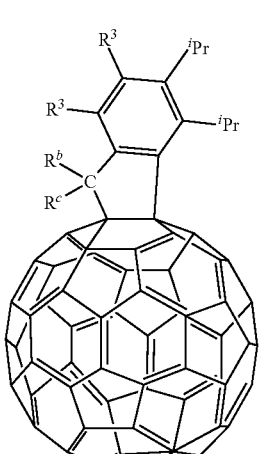

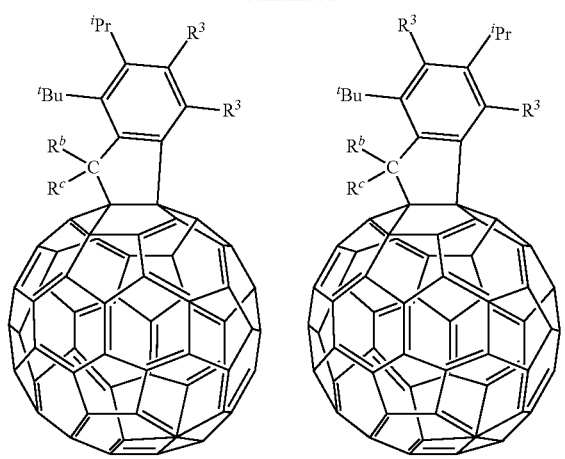
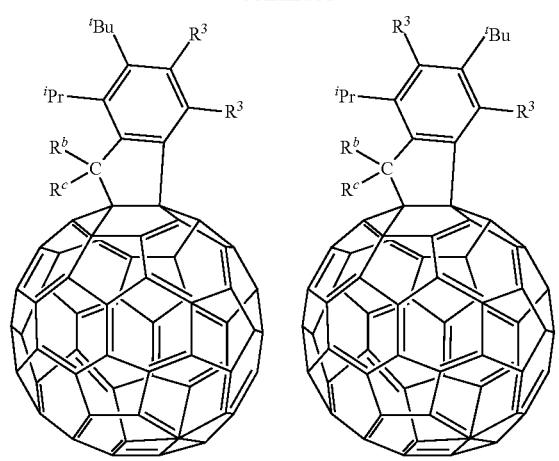
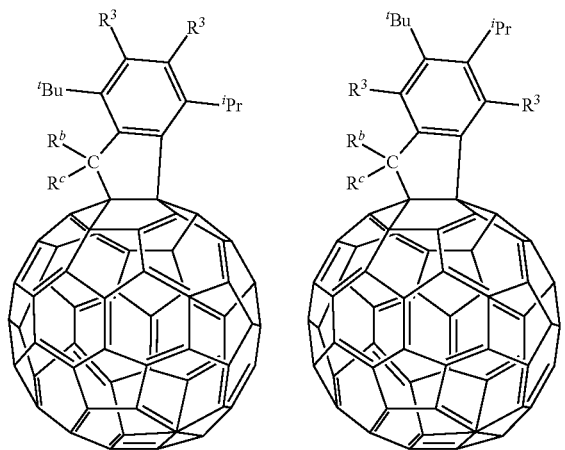
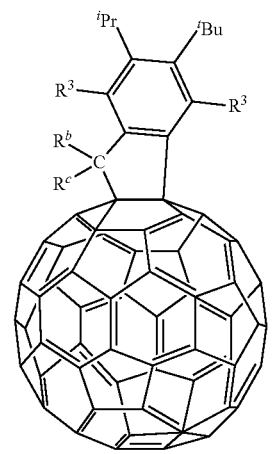
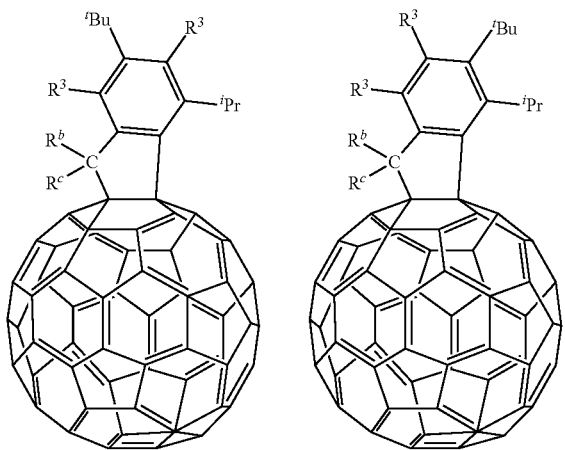
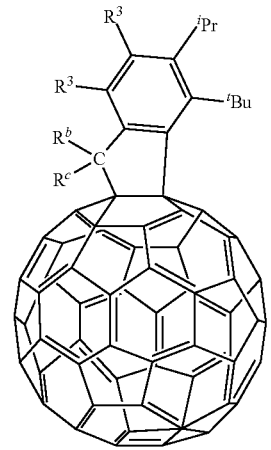

37
-continued
38
-continued
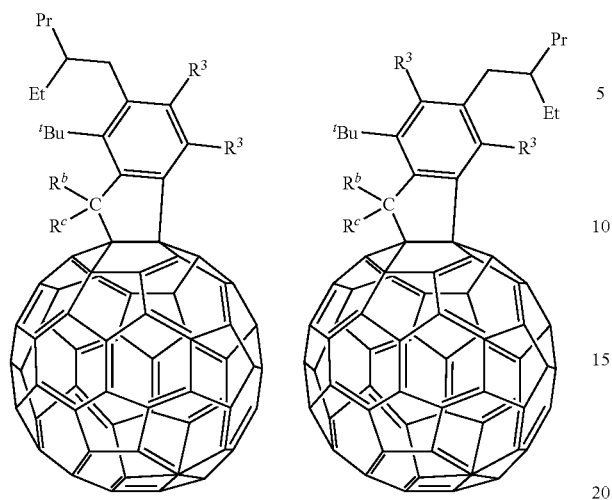
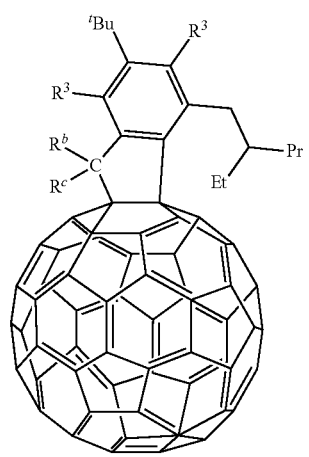
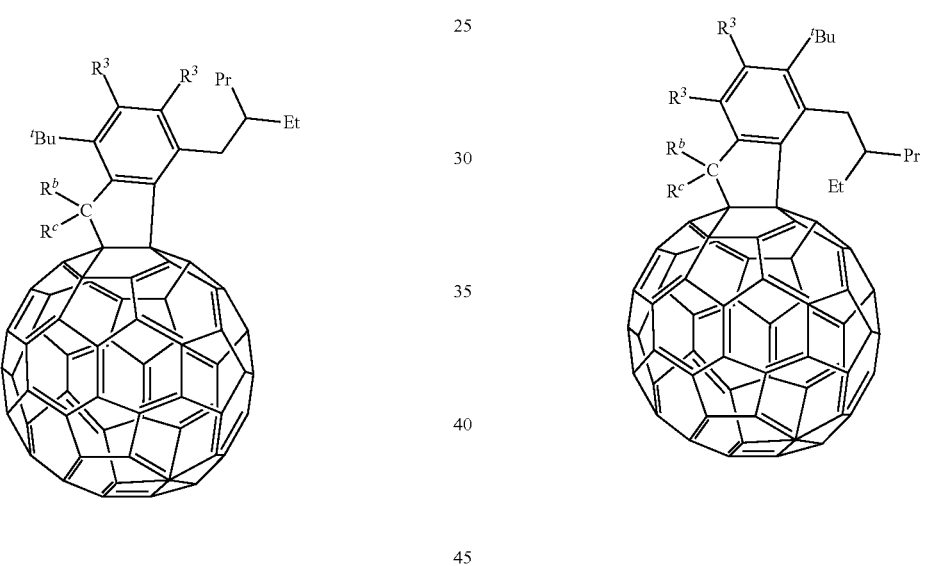
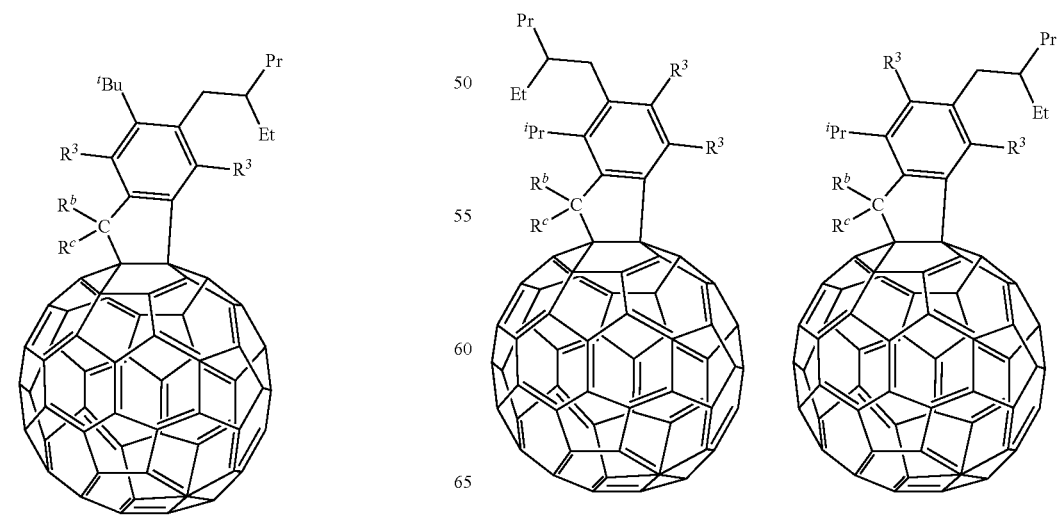

-continued
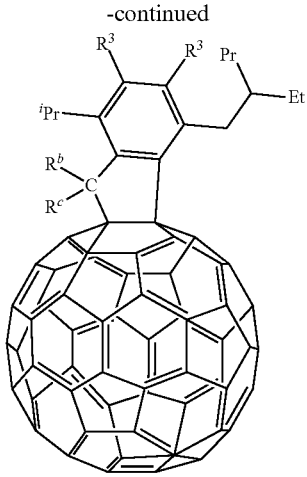
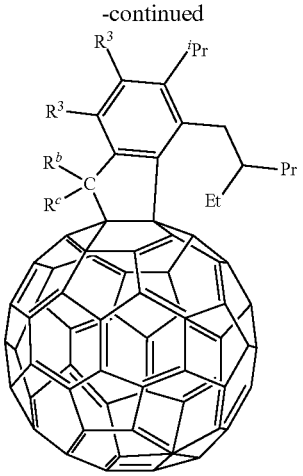
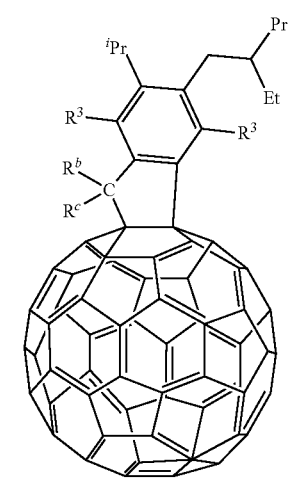
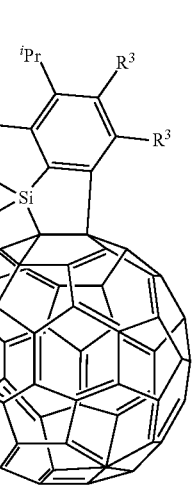 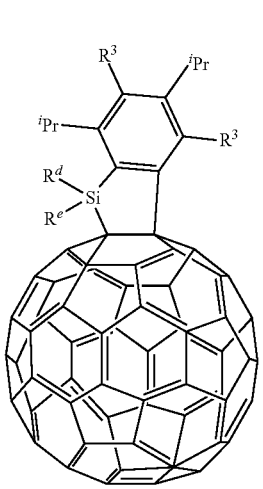
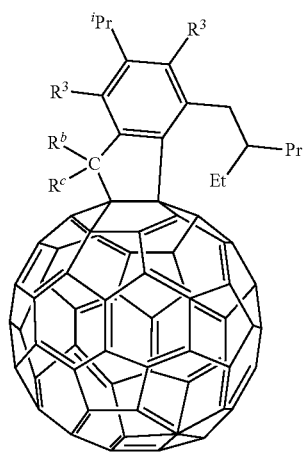
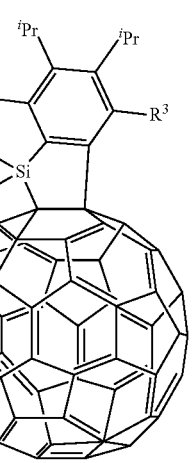

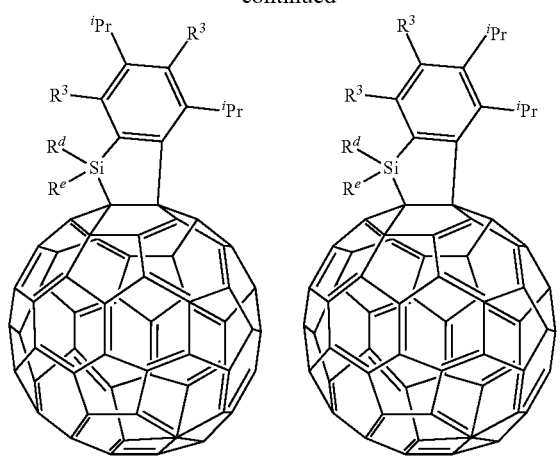
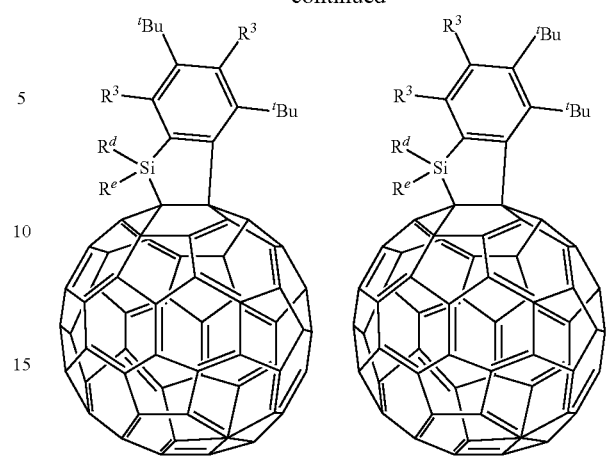
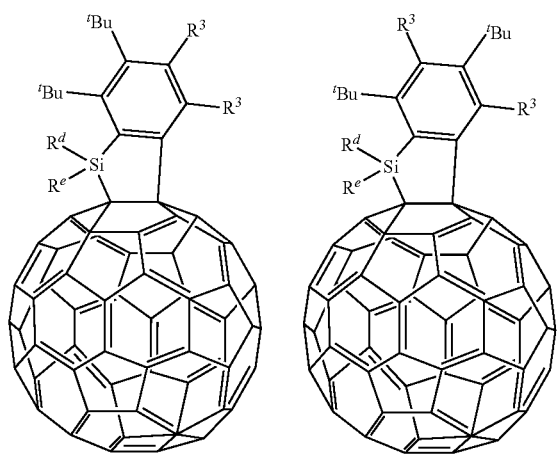
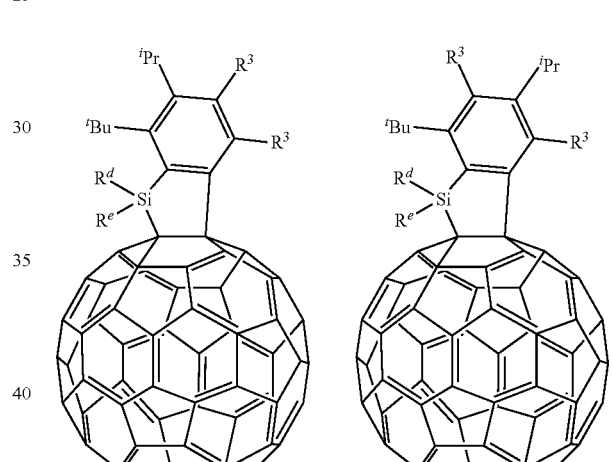
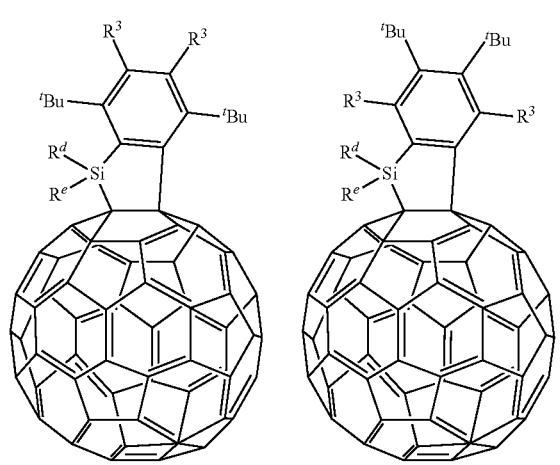
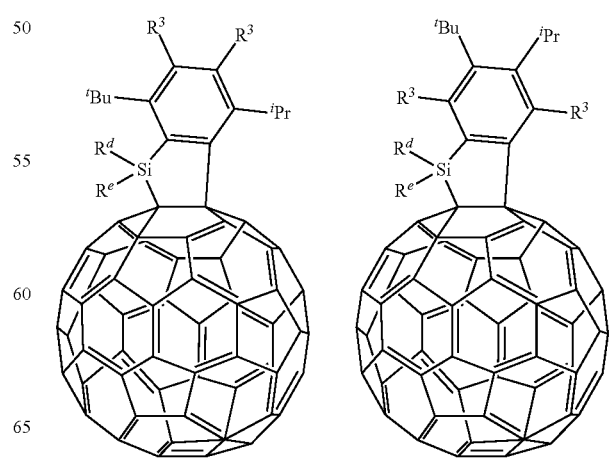

-continued
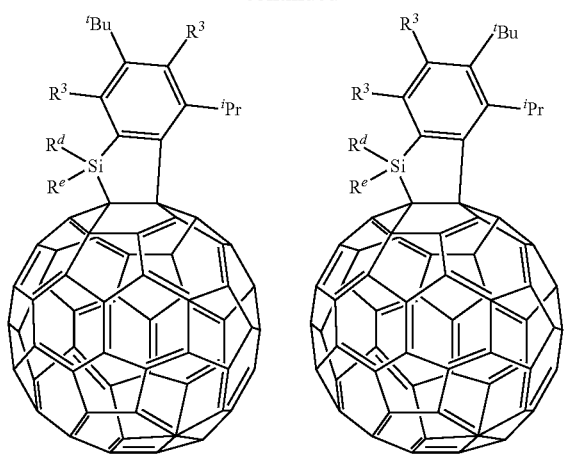
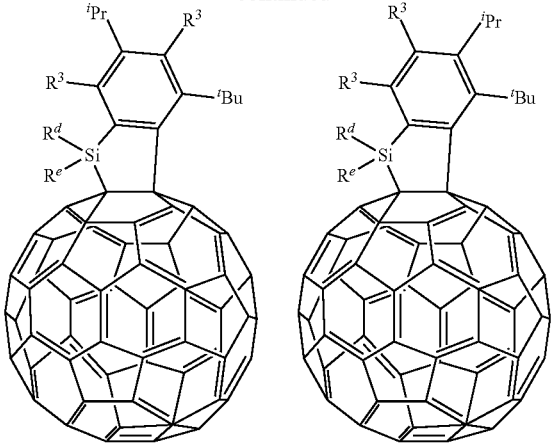
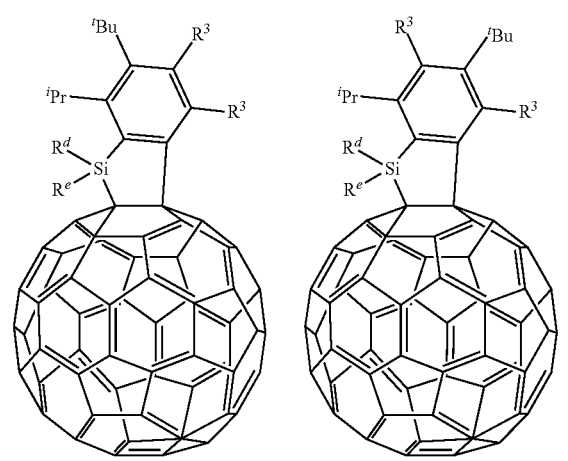
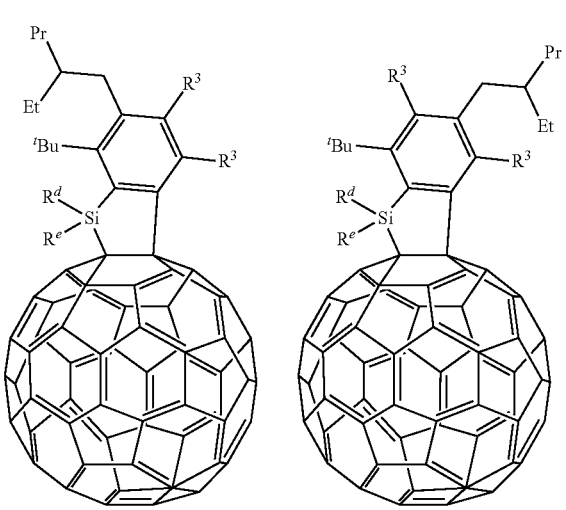
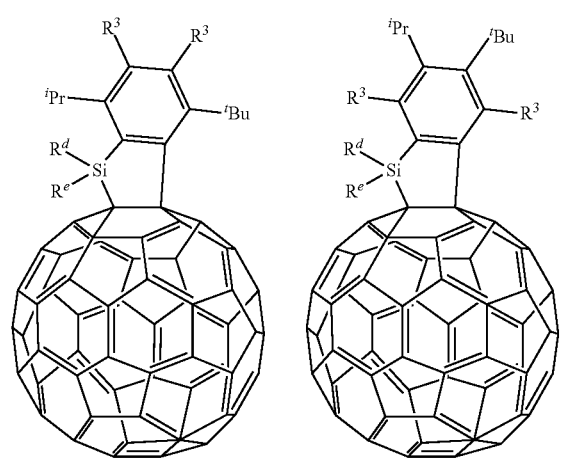
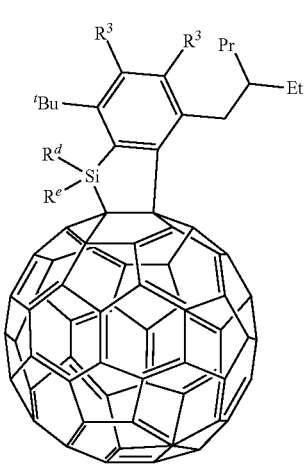

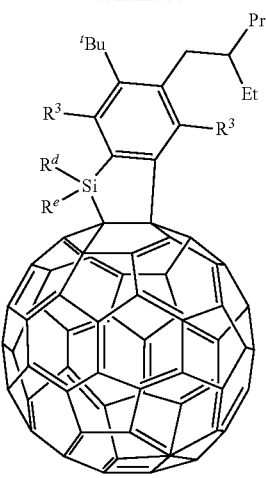
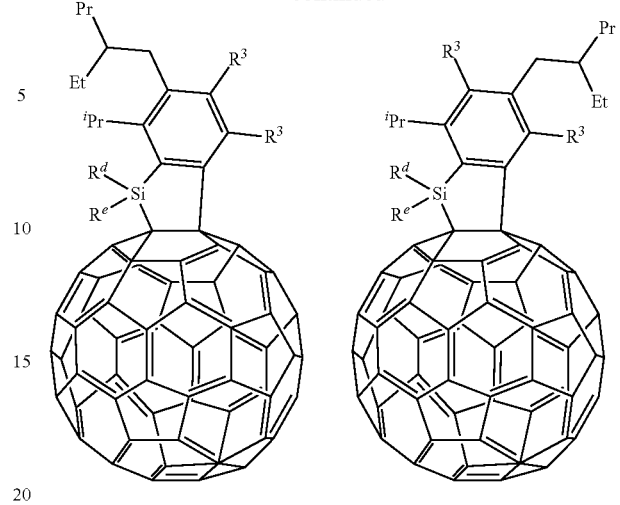
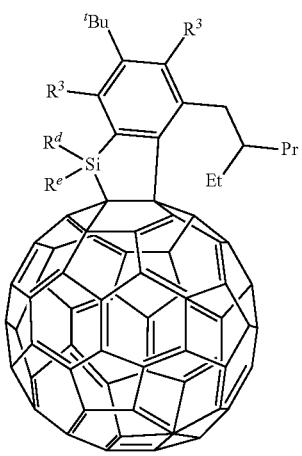
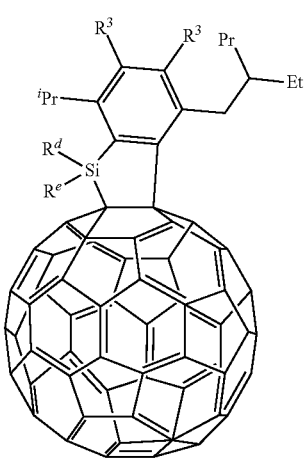
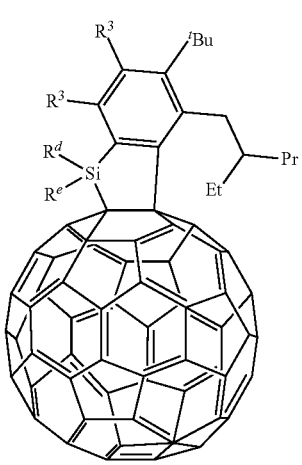
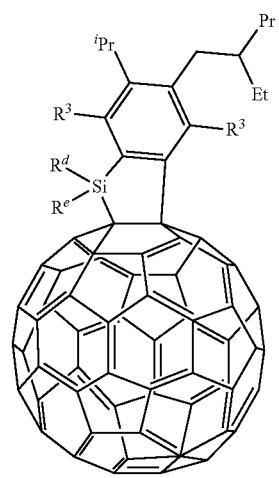

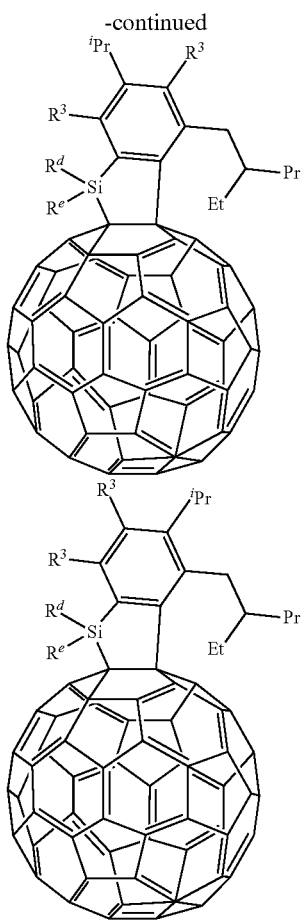

In Group 1, i-Pr is isopropyl, t-Bu is t-butyl, Pr is n-propyl, and Et is ethyl.

The fullerene derivative may be vacuum-deposited through sublimation into a thin film as described above. The thin film may maintain inherent characteristics of the fullerene derivative without breaking and/or transforming a chemical bond of the fullerene derivative, and accordingly, transformation of optical properties of the thin film may be reduced, compared with transformation of the optical properties due to an aggregation during deposition of a thin film including an unsubstituted fullerene (e.g., C60). For example, the thin film including the fullerene derivative may have different light absorption characteristics from those of a thin film including unsubstituted fullerene (e.g., C60 fullerene), and for example, abnormal light absorption of the thin film including the fullerene derivative may be decreased in a short wavelength region of visible ray of about 400 nm to about 500 nm. For example, the film including the fullerene derivative may have a smaller extinction coefficient at a wavelength of 450 nm than that of the thin film including unsubstituted fullerene (e.g., C60 fullerene), for example, less than or equal to about ½ of the extinction coefficient of the thin film including unsubstituted fullerene (e.g., C60 fullerene).

Hereinafter, a photoelectric device including the fullerene derivative is described.

FIG. 1 is a cross-sectional view showing a photoelectric device according to an embodiment.

Referring to FIG. 1, a photoelectric device 100 according to an embodiment includes a first electrode 10 and a second electrode 20 facing each other and an organic layer 30 disposed between the first electrode 10 and the second electrode 20.

A substrate (not shown) may be disposed on a surface of the first electrode 10 or a surface of the second electrode 20. The substrate may be for example made of an inorganic material such as glass, an organic material such as polycarbonate, polymethylmethacrylate, polyethyleneterephthalate, polyethylenenaphthalate, polyamide, polyethersulfone, or a combination thereof, or a silicon wafer. The substrate may be omitted.

One of the first electrode 10 and the second electrode 20 may be an anode and the other may be a cathode. For example, the first electrode 10 may be an anode and the second electrode 20 may be a cathode.

At least one of the first electrode 10 and the second electrode 20 may be a light-transmitting electrode and the light-transmitting electrode may be for example made of a conductive oxide such as an indium tin oxide (ITO), indium zinc oxide (IZO), zinc oxide (ZnO), tin oxide ($SnO_2$), aluminum tin oxide (AlTO), and fluorine doped tin oxide (FTO), or a metal thin layer of a single layer or a multilayer. When one of the first electrode 10 and the second electrode 20 is a non-light-transmitting electrode, it may be made of for example an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The organic layer 30 may include an active layer.

The active layer is a layer including a p-type semiconductor and an n-type semiconductor to provide a pn junction, which is a layer producing excitons by receiving light from outside and then separating holes and electrons from the produced excitons.

The p-type semiconductor and the n-type semiconductor may be light absorbing materials that absorb at least one part of light in each visible light region and for example the p-type semiconductor may be a light absorbing material that may mainly and selectively absorb light in one of wavelength regions of greater than or equal to about 400 nm and less than about 500 nm, about 500 nm to about 600 nm, and/or greater than about 600 nm and less than or equal to about 700 nm, and the n-type semiconductor may be the fullerene derivative.

For example, the p-type semiconductor may be a light absorbing material that may mainly and selectively absorb light in a wavelength region of greater than or equal to about 400 nm and less than 500 nm, about 500 nm to about 600 nm, and greater about 600 nm and less than or equal to about 700 nm, and the n-type semiconductor may be a fullerene derivative. For example, the p-type semiconductor may be a light absorbing material that may mainly and selectively absorb light in a wavelength region of about 500 nm to about 600 nm and the n-type semiconductor may be the fullerene derivative.

For example, the p-type semiconductor may be for example a light absorbing material having a LUMO energy level of about 3.0 eV to about 3.6 eV and a HOMO energy level of about 5.1 eV to about 5.7 eV. Within the ranges, the p-type semiconductor may be for example a light absorbing material having a LUMO energy level of about 3.1 eV to about 3.5 eV and a HOMO energy level of about 5.2 eV to about 5.6 eV.

For example, the p-type semiconductor may be for example a light absorbing material having a core structure including an electron donating moiety, a pi conjugation linking group, and an electron accepting moiety.

The p-type semiconductor is a compound having the core structure and may include for example a compound represented by Chemical Formula 4, but is not limited thereto.

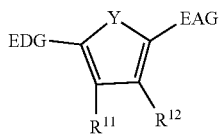

[Chemical Formula 4]

In Chemical Formula 4,

Y is Se, Te, S, SO, SO$_2$, or SiR$^h$R$^i$,

EDG is an electron donating group,

EAG is an electron accepting group, and

R$^{11}$, R$^{12}$, R$^h$, and R$^i$ are independently hydrogen or a monovalent substituent.

Herein, the monovalent substituent may be for example a substituted or unsubstituted C1 to C30 alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, but is not limited thereto.

The p-type semiconductor may be for example a light absorbing material represented by Chemical Formula 4A, but is not limited thereto.

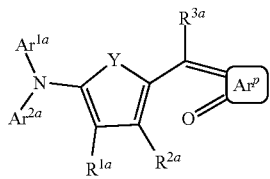

[Chemical Formula 4A]

In Chemical Formula 4A,

Y is Se, Te, S, SO, SO$_2$, or SiR$^h$R$^i$,

Ar$^p$ is a substituted or unsubstituted 5-membered ring, a substituted or unsubstituted 6-membered ring, or a condensed ring of two or more of the foregoing rings, Ar$^{1a}$ and Ar$^{2a}$ are independently a substituted or unsubstituted C6 to C30 aryl group or a substituted or unsubstituted C3 to C30 heteroaryl group, Ar$^{1a}$ and Ar$^{2a}$ are independently present or linked with each other by a linker of G$^1$ to form a ring, wherein G$^1$ is one of a single bond, —(CR$^j$R$^k$)$_{n2}$—, —O—, —S—, —Se—, —N=, —NR$^l$—, —SiR$^m$R$^n$—, and —GeR$^o$R$^p$— and n2 is 1 or 2, and R$^{1a}$ to R$^{3a}$ and R$^h$ to R$^p$ are independently hydrogen, a substituted or unsubstituted C1 to C30 an alkyl group, a substituted or unsubstituted C6 to C30 aryl group, a substituted or unsubstituted C3 to C30 heteroaryl group, a substituted or unsubstituted C1 to C30 alkoxy group, a halogen, a cyano group, or a cyano-containing group.

The p-type semiconductor may be for example a light absorbing material represented by one of Chemical Formulae 2A-1 to 2A-4, but is not limited thereto.

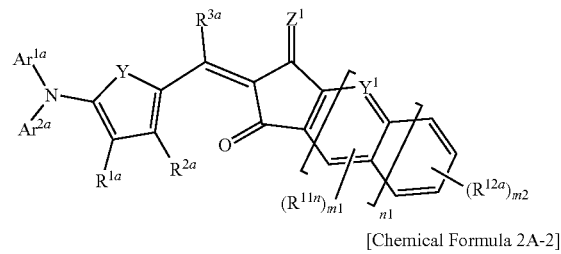

[Chemical Formula 2A-1]

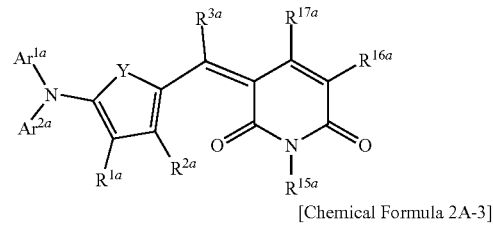

[Chemical Formula 2A-2]

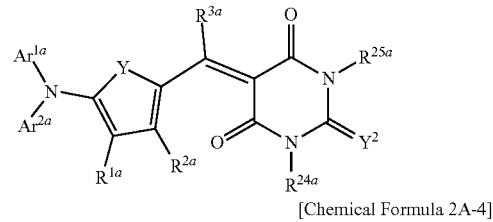

[Chemical Formula 2A-3]

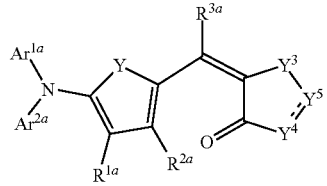

[Chemical Formula 2A-4]

In Chemical Formulae 2A-1 to 2A-4,

Y is Se, Te, S, SO, SO$_2$, or SiR$^h$R$^i$,

Z$^1$ is O or CR$^q$R$^r$,

Y$^1$ is N or CR$^s$,

Y$^2$ is one of O, S, Se, Te, and C(R$^t$)(CN),

Y$^3$ is O, S, Se, or Te,

Y$^4$ is N or NR$^{18a}$,

Y$^5$ is CR$^{19a}$ or C=CR$^{20a}$ (CN),

Ar$^{1a}$ and Ar$^{2a}$ are independently a substituted or unsubstituted C6 to C30 aryl group or a substituted or unsubstituted C3 to C30 heteroaryl group, Ar$^{1a}$ and Ar$^{2a}$ are independently present or linked with each other to form a ring, R$^{1a}$ to R$^{3a}$, R$^{11a}$, R$_{12a}$, R$^{15a}$ to R$^{20a}$, R$^{24a}$, R$^{25a}$, R$^h$, R$^i$, and R$^q$ to R$^t$ are independently hydrogen, a substituted or unsubstituted C1 to C30 an alkyl group, a substituted or unsubstituted C6 to C30 aryl group, a substituted or unsubstituted C3 to C30 heteroaryl group, a substituted or unsubstituted C1 to C6 alkoxy group, a halogen, or a cyano group, n1 is 0 or 1, m1 is 0 or 1, and m2 is an integer ranging from 0 to 4.

The light absorbing material represented by one of Chemical Formulae 2A-1 to 2A-4 may be for example one of compounds of Group 2 to Group 5, but is not limited thereto.

[Group 2]
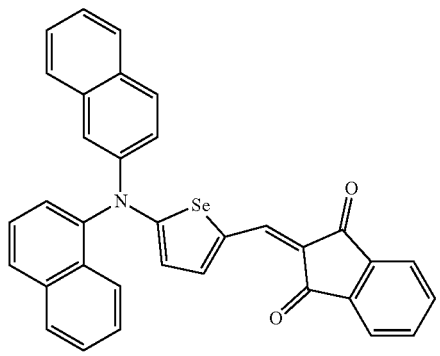
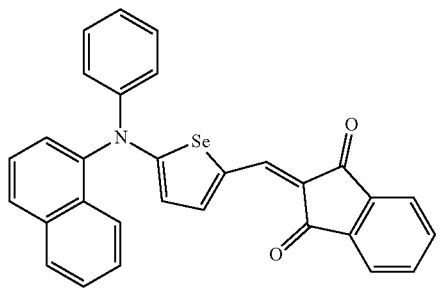
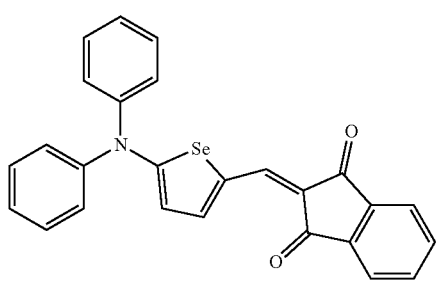
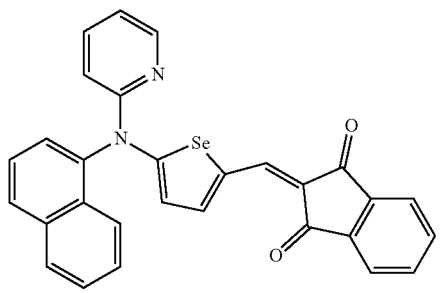
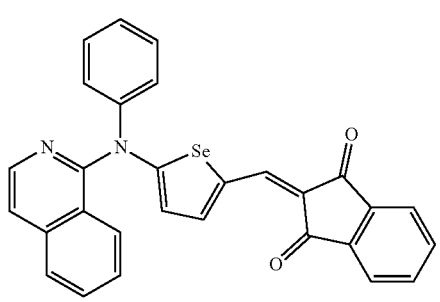
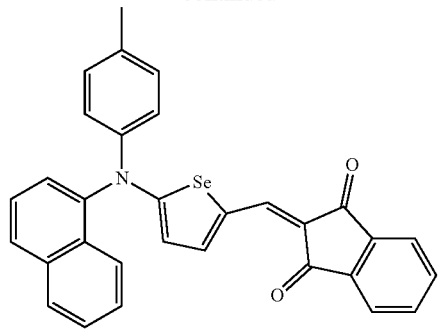
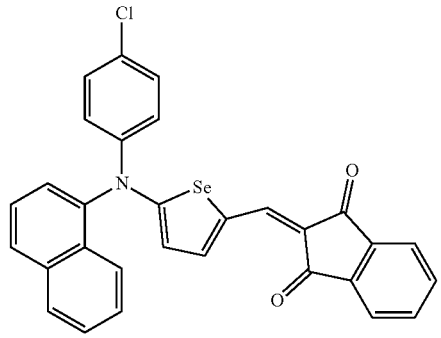
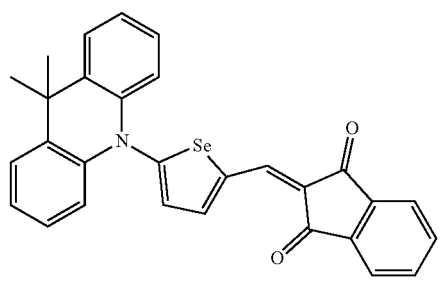
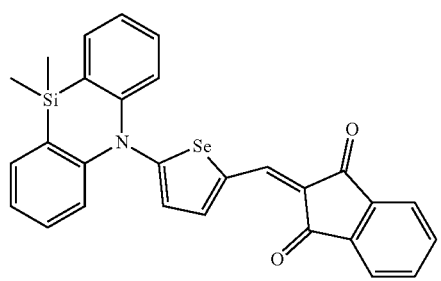
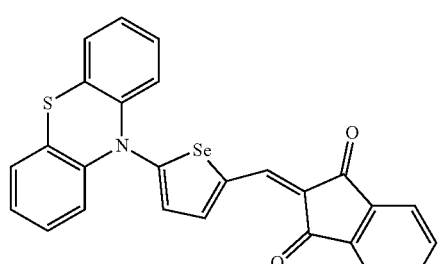

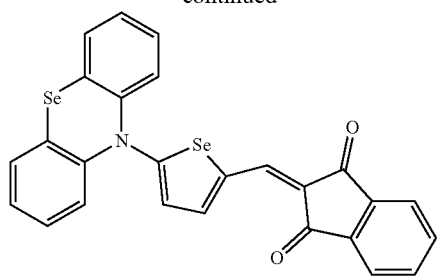
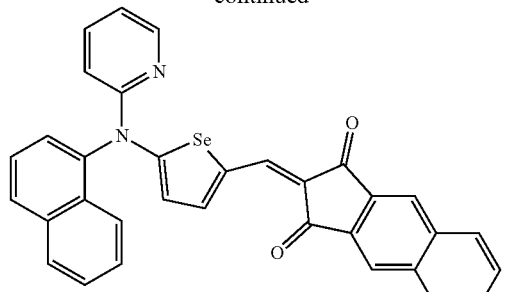
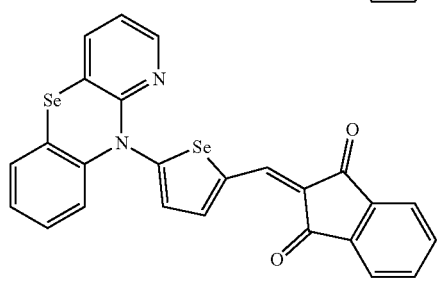
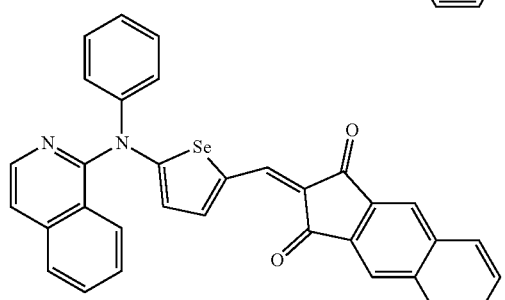
[Group 3]
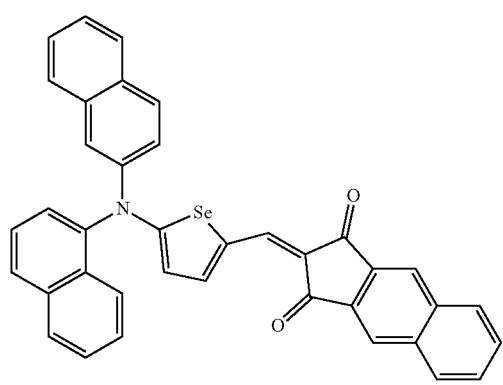
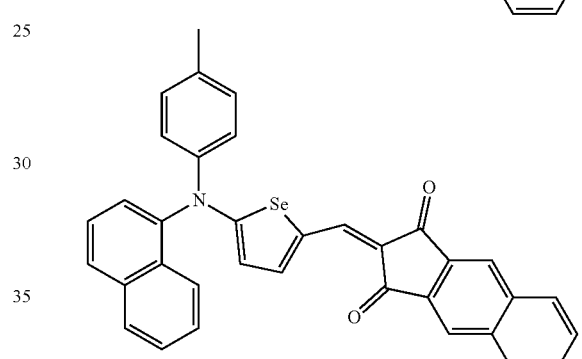
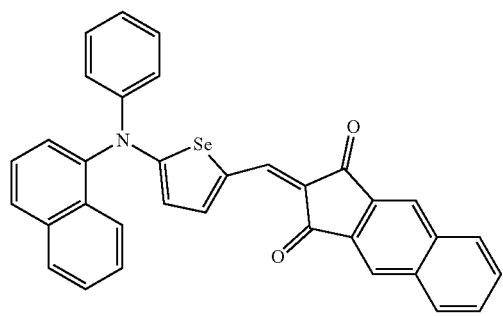
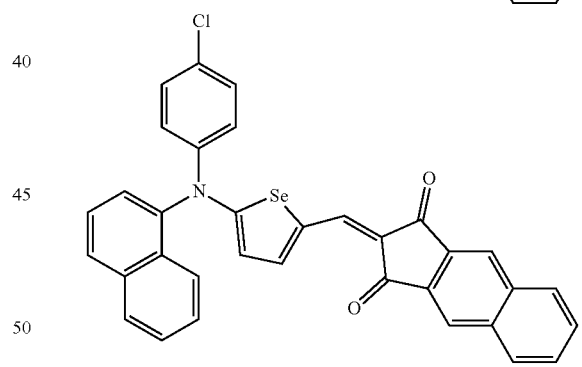
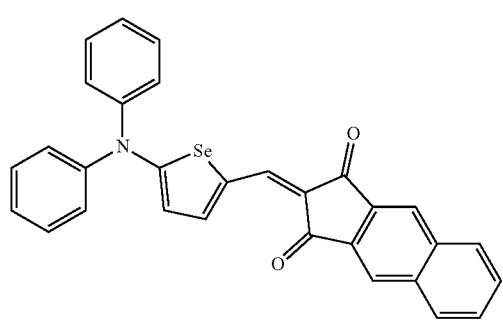
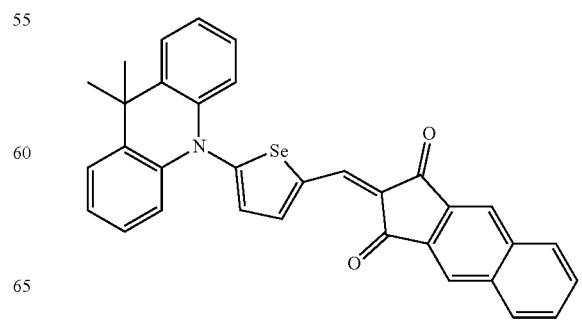

-continued
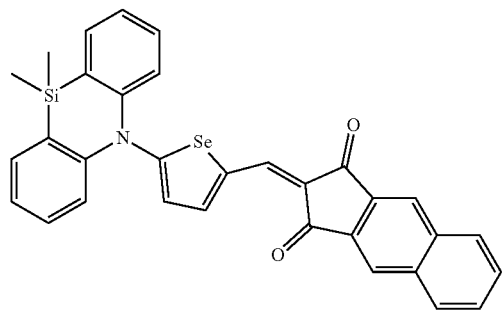
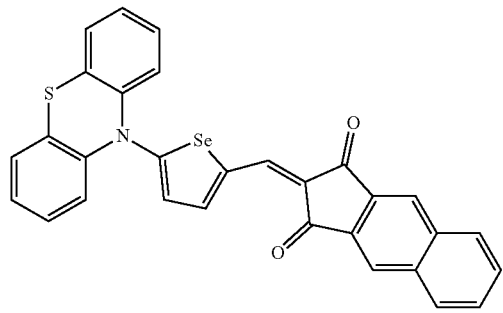
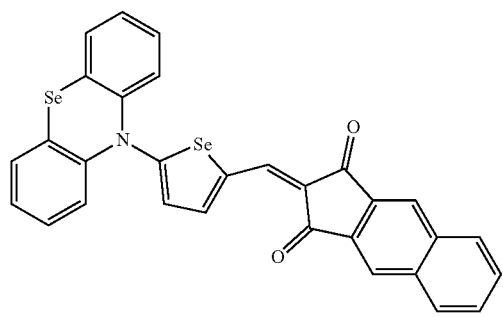
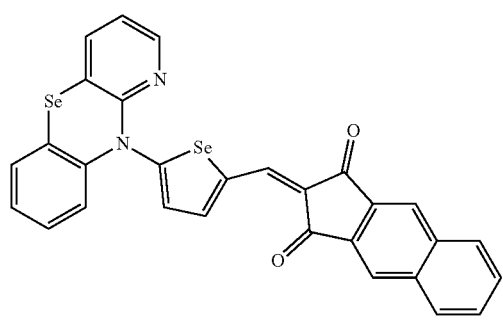
[Group 4]
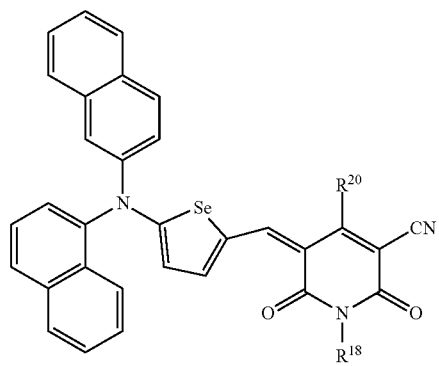
-continued
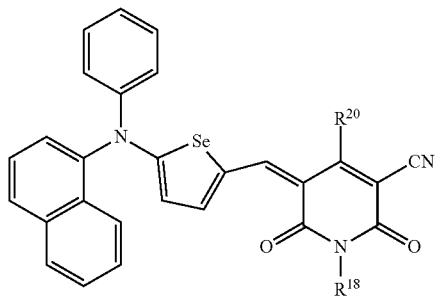
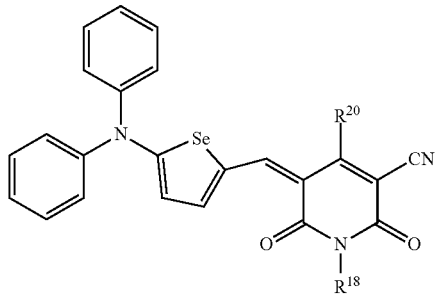
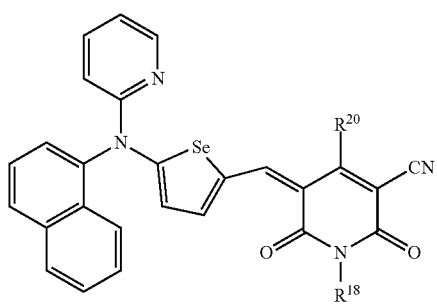
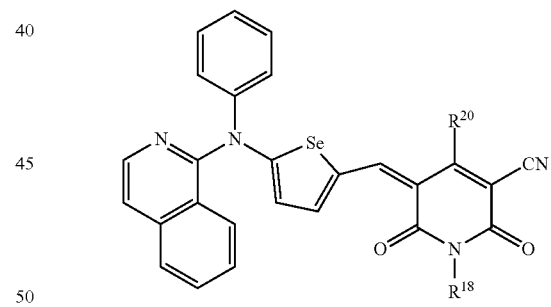
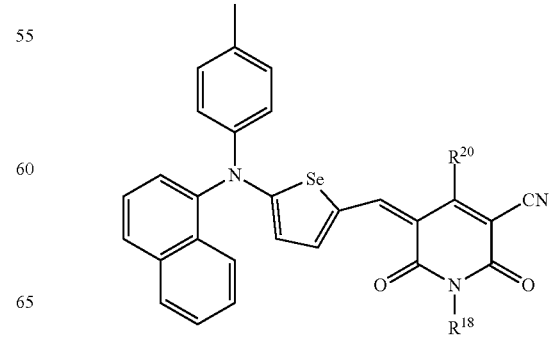

-continued
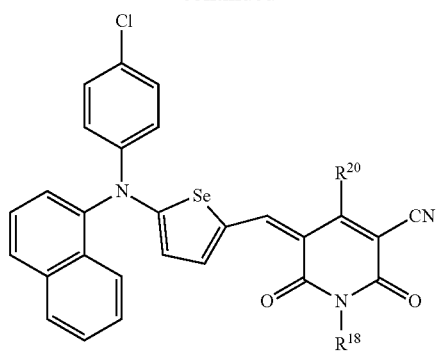
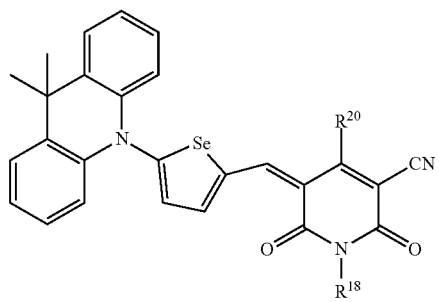
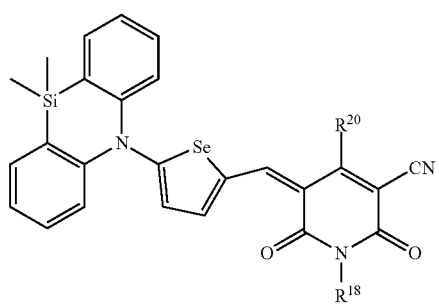
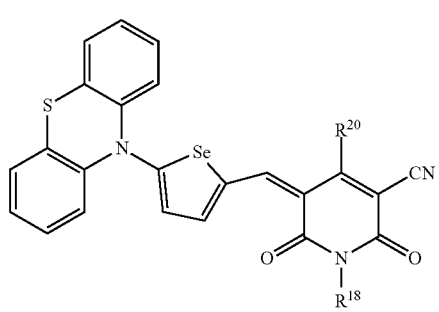
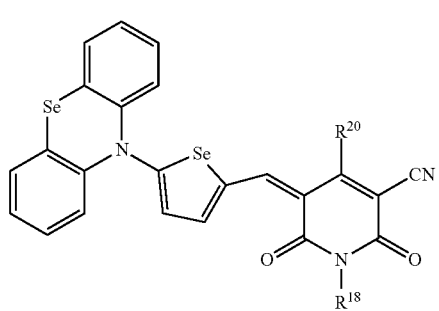
-continued
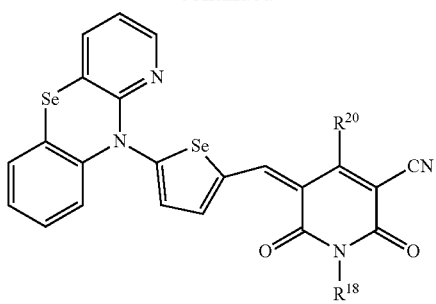
[Group 5]
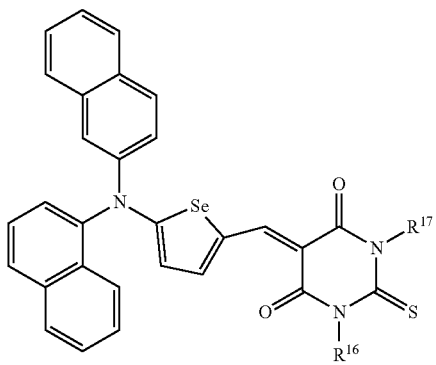
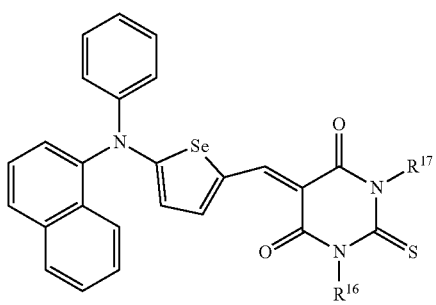
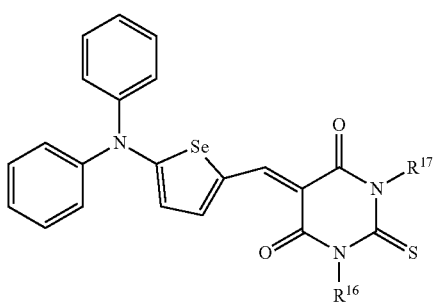
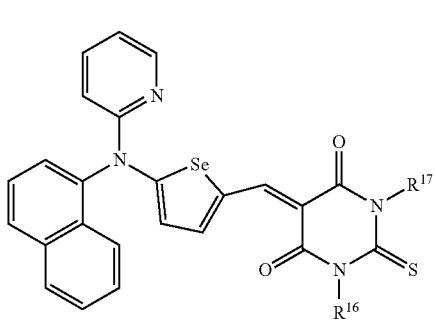

-continued

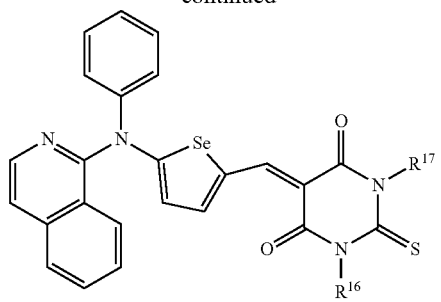
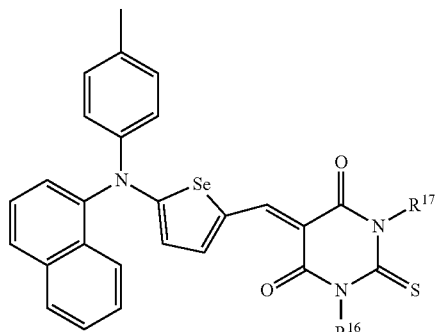
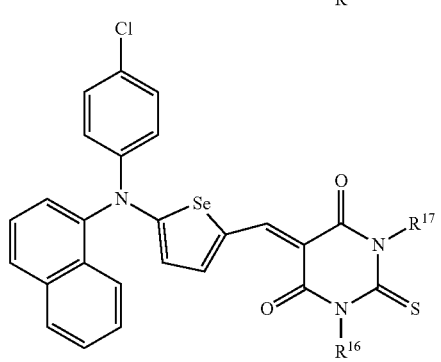
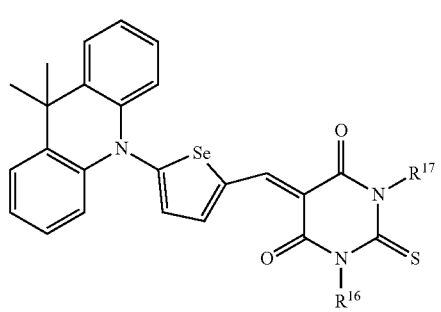
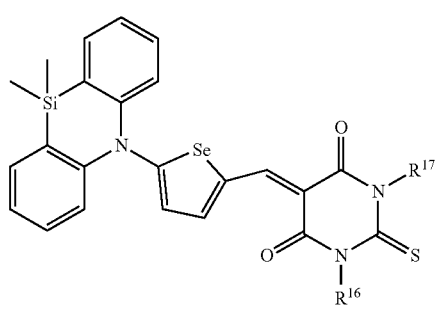

-continued

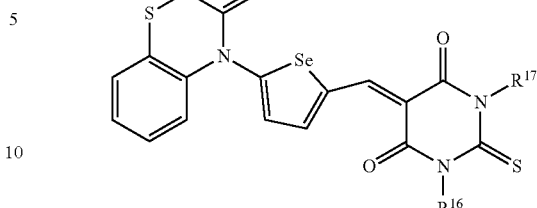
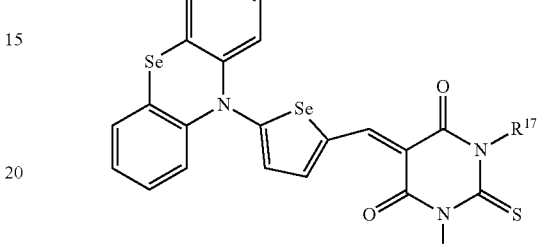
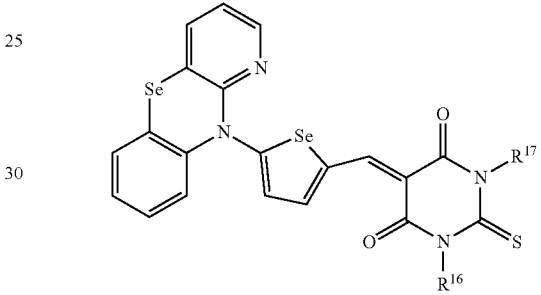

In Groups 2 to 5, hydrogen of each aromatic ring may be replaced by a substituent selected from a substituted or unsubstituted C1 to C30 alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, and a combination thereof, and $R^{16}$, $R^{17}$, $R^{18}$, and $R^{20}$ are independently hydrogen, a substituted or unsubstituted C1 to C30 an alkyl group, a substituted or unsubstituted C1 to C30 alkoxy group, a substituted or unsubstituted C6 to C30 aryl group, a substituted or unsubstituted C4 to C30 heteroaryl group, a halogen, a cyano group, a cyano-containing group, or a combination thereof.

The n-type semiconductor may include the fullerene derivative.

The fullerene derivative may electrically match with the p-type semiconductor effectively and may have for example a LUMO energy level of about 3.7 eV to about 5.0 eV and a HOMO energy level of about 5.8 eV to about 7.0 eV. Within the ranges, for example it may have a LUMO energy level of about 3.8 eV to about 4.9 eV and a HOMO energy level of about 6.0 eV to about 6.9 eV, a LUMO energy level of about 3.8 eV to about 4.8 eV and a HOMO energy level of about 6.0 eV to about 6.7 eV, or a LUMO energy level of about 3.8 eV to about 4.5 eV and a HOMO energy level of about 6.0 eV to 6.5 eV. The fullerene derivative may have for example an energy band gap of about 2.0 eV to about 2.3 eV. When the fullerene derivative has an energy level within the ranges, it may play an effective role of an n-type semiconductor with the p-type semiconductor.

The fullerene derivative may be designed as long as it satisfies the electrical characteristics and specific structures of the fullerene derivative described above.

The fullerene derivative is effectively electrically matched with the p-type semiconductor as described above. In addition, the fullerene derivative has a structure substituted with a fused ring of a pentagonal ring and an aromatic ring and thus may increase a steric hindrance but decrease a π-conjugation system compared with the unsubstituted fullerene. Accordingly, the fullerene derivative may suppress an aggregation during the deposition compared with the unsubstituted C60 fullerene and thus may improve film-formation characteristics and reduce deformation of optical properties such as a deformation of an absorption wavelength region which may be caused by the aggregation.

The above p-type semiconductor and an n-type semiconductor including the fullerene derivative may be codeposited through sublimation to form an active layer, and thus the active layer may maintain inherent characteristics of the fullerene derivative without breaking and/or transforming a chemical bond of the fullerene derivative during the codeposition.

For example, the active layer including the fullerene derivative may have different light absorption characteristics from those of an active layer including unsubstituted fullerene (e.g., C60 fullerene), and thus abnormal absorption in a short wavelength region of a visible ray, for example, ranging from about 400 nm to about 500 nm may be reduced. For example, the active layer including the fullerene derivative may have a smaller extinction coefficient at a wavelength of 450 nm than that of an active layer including unsubstituted fullerene (e.g., C60 fullerene), and the extinction coefficient of the active layer including the fullerene derivative may be less than or equal to about ½ of that of the active layer including unsubstituted fullerene (e.g., C60 fullerene) at a wavelength of 450 nm.

Light absorption characteristics of the active layer may be expressed by combining those of the p-type semiconductor with those of the n-type semiconductor. For example, an absorption peak of an active layer including a p-type semiconductor selectively absorbing light in a wavelength region of about 500 nm to about 600 nm and an n-type semiconductor including the fullerene derivative may be easily separated compared with that the active layer including the p-type semiconductor selectively absorbing light in a wavelength region of about 500 nm to about 600 nm and an unsubstituted fullerene (e.g., C60 fullerene), and thus wavelength selectivity of the active layer may be increased. Accordingly, the active layer may be effectively used for a photoelectric device requiring the wavelength selectivity.

The active layer may include an intrinsic layer (I layer) formed by codepositing the p-type semiconductor and the n-type semiconductor including the fullerene derivative and the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The active layer may further include a p-type layer and/or an n-type layer in addition to the intrinsic layer. The p-type layer may include the p-type semiconductor and the n-type layer may include the n-type semiconductor. For example, the active layer may include various combinations of a p-type layer/an I layer, an I layer/an n-type layer, a p-type layer/an I layer/a n-type layer, and the like.

The organic layer 30 may further include a charge auxiliary layer (not shown) between the first electrode 10 and the active layer and/or between the second electrode 20 and the active layer.

The charge auxiliary layer may make holes and electrons separated in the active layer 30 be transported easily to improve efficiency.

The charge auxiliary layer may include at least one selected from a hole injection layer for facilitating hole injection, a hole transport layer for facilitating hole transport, an electron blocking layer for preventing electron transport, an electron injection layer for facilitating electron injection, an electron transport layer for facilitating electron transport, and a hole blocking layer for preventing hole transport.

The charge auxiliary layer may include for example an organic material, an inorganic material, or an organic/inorganic material. The organic material may be an organic material having hole or electron injection, transportation and/or blocking characteristics and the inorganic material may be for example a metal oxide such as a molybdenum oxide, a tungsten oxide, or a nickel oxide.

The charge auxiliary layer may include for example the fullerene derivative.

The photoelectric device 100 may further include an anti-reflection layer (not shown) on one surface of the first electrode 10 or the second electrode 20. The anti-reflection layer is disposed at a light incidence side and lowers reflectance of light of incident light and thereby light absorbance is further improved. For example, when light enters from the first electrode 10, the anti-reflection layer may be disposed on the first electrode 10 while when light enters from the second electrode 20, the anti-reflection layer may be disposed under the second electrode 20.

The anti-reflection layer may include, for example a material having a refractive index of about 1.6 to about 2.5, and may include for example at least one of a metal oxide, a metal sulfide, and an organic material having a refractive index within the ranges. The anti-reflection layer may include, for example a metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as zinc sulfide; or an organic material such as an amine derivative, but is not limited thereto.

In the photoelectric device 100, when light enters from the first electrode 10 or second electrode 20 and the active layer 30 absorbs light in a predetermined (and/or alternatively desired) wavelength region, excitons may be produced from the inside. The excitons are separated into holes and electrons in the active layer in the organic layer 30, and the separated holes are transported to an anode that is one of the first electrode 10 and the second electrode 20 and the separated electrons are transported to the cathode that is the other of the first electrode 10 and the second electrode 20 so as to flow a current.

The photoelectric device 100 may be applied to a solar cell, an image sensor, a photodetector, a photosensor, and an organic light emitting diode (OLED), but is not limited thereto.

The photoelectric device may be for example applied to an image sensor.

Hereinafter, an example of an image sensor including the photoelectric device is described referring to drawings. As an example of an image sensor, an organic CMOS image sensor is described.

Figure 2:
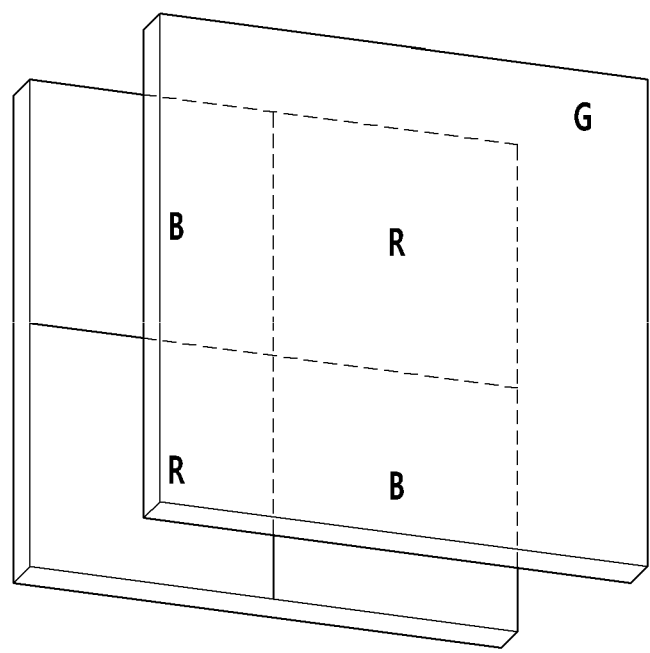
FIG. 2 is a schematic top plan view showing an organic CMOS image sensor according to an embodiment.
Figure 3:
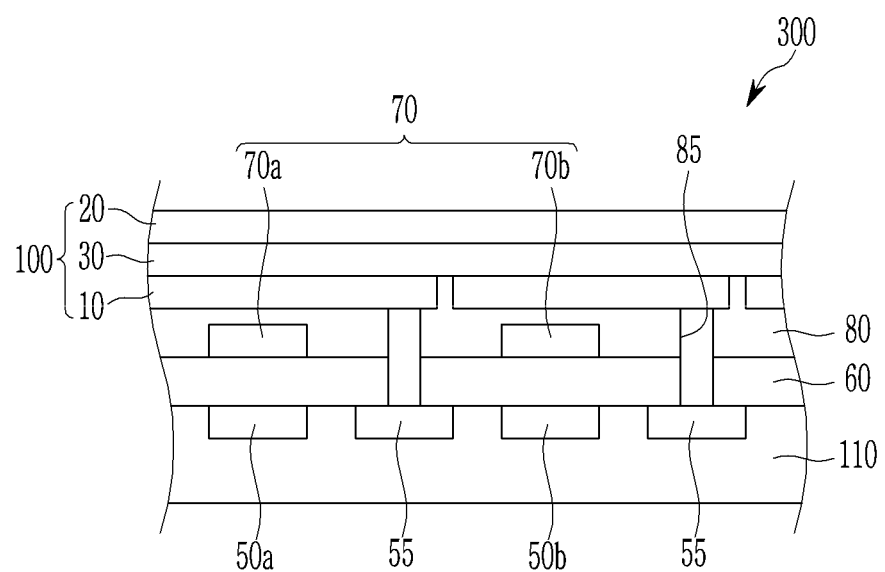
FIG. 3 is a cross-sectional view showing one example of the organic CMOS image sensor of FIG. 2.

FIG. 2 is a schematic top plan view of an organic CMOS image sensor according to an embodiment and FIG. 3 is a cross-sectional view showing one example of the organic CMOS image sensor of FIG. 2.

Referring to FIGS. 2 and 3, an organic CMOS image sensor 300 according to an example embodiment includes a semiconductor substrate 110 integrated with photo-sensing devices 50a and 50b, a transmission transistor (not shown) and a charge storage 55, a lower insulation layer 60, a color filter layer 70, an upper insulation layer 80, and a photoelectric device 100.

The semiconductor substrate 110 may be a silicon substrate, and is integrated with the photo-sensing devices 50a and 50b, the transmission transistor (not shown), and the charge storage 55. The photo-sensing devices 50a and 50b may be photodiodes.

The photo-sensing devices 50a and 50b, the transmission transistor, and/or the charge storage 55 may be integrated in each pixel, and as shown in the drawing, the photo-sensing devices 50a and 50b may be respectively included in a blue pixel and a red pixel and the charge storage 55 may be included in a green pixel.

The photo-sensing devices 50a and 50b sense light, the information sensed by the photo-sensing devices may be transferred by the transmission transistor, the charge storage 55 is electrically connected to the photoelectric device 100 that will be described later, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing device 50a and 50b.

The lower insulation layer 60 is formed on the metal wire and the pad. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench exposing the charge storage 55. The trench may be filled with fillers.

A color filter layer 70 is formed on the lower insulation layer 60. The color filter layer 70 includes a blue filter 70a formed in a blue pixel and a red filter 70b formed in a red pixel. In the present embodiment, a green filter is not included, but a green filter may be further included.

The upper insulation layer 80 is formed on the color filter layer 70. The upper insulation layer 80 eliminates a step caused by the color filter layer 70 and smoothens the surface. The upper insulation layer 80 and the lower insulation layer 60 may include a contact hole (not shown) exposing a pad, and a through-hole 85 exposing the charge storage 55 of the green pixel.

The photoelectric device 100 is formed on the upper insulation layer 80. The photoelectric device 100 includes the first electrode 10, the organic layer 30, and the second electrode 20 as described above. In the drawing, the first electrode 10, the organic layer 30, and the second electrode 20 are sequentially stacked, but this disclosure is not limited thereto, and for example they may be stacked in an order of the second electrode 20, the organic layer 30, and the first electrode 10.

The first electrode 10 and the second electrode 20 may be all light-transmitting electrodes and the organic layer 30 is the same as described above. The organic layer 30 may for example selectively absorb light in a green wavelength region and may replace a color filter of a green pixel.

Light in a green wavelength region of light that enters from the second electrode 20 is mainly absorbed by the organic layer 30 and photoelectrically converted and light in a remaining wavelength region is transmitted through the first electrode 10 and is sensed by the photo-sensing devices 50a and 50b.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

As described above, the photoelectric device 100 has a stack structure thereby a size of an image sensor may be reduced to realize a down-sized image sensor.

In addition, the organic layer includes the fullerene derivative having optical absorption characteristics shifted toward a short wavelength as described above and thus may increase wavelength selectivity compared with the one including the unsubstituted C60 fullerene.

The photoelectric device selectively absorbing light in a green wavelength region is for example stacked but this disclosure is not limited thereto. For example, a photoelectric device selectively absorbing light in a blue wavelength region may be stacked and a green photo-sensing device and a red photo-sensing device may be integrated in the semiconductor substrate 110 or a photoelectric device selectively absorbing light in a red wavelength region may be stacked and a green photo-sensing device and a blue photo-sensing device may be integrated in the semiconductor substrate 110.

Figure 4:
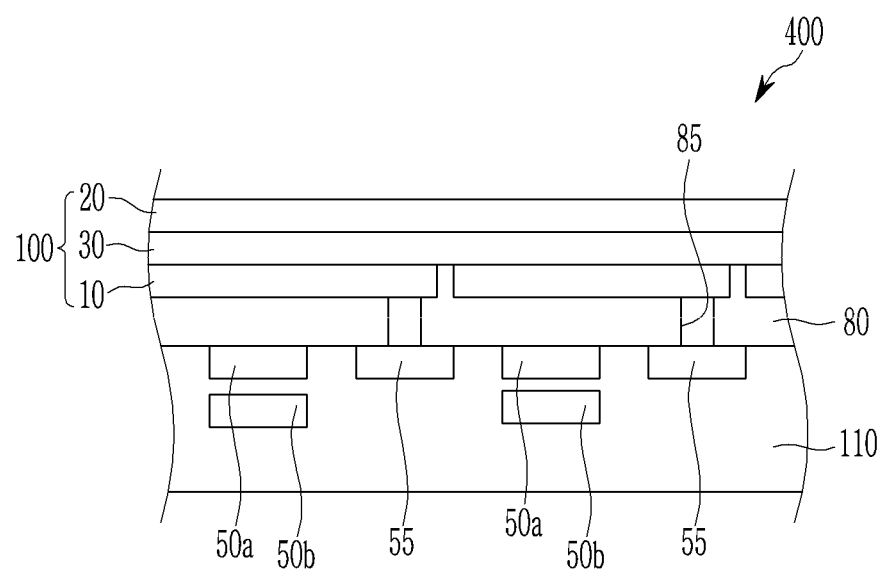
FIG. 4 is a cross-sectional view showing another example of the organic CMOS image sensor.

FIG. 4 is a cross-sectional view showing another example of the organic CMOS image sensor.

Like the above embodiment, the organic CMOS image sensor 400 according to the present embodiment includes a semiconductor substrate 110 integrated with photo-sensing devices 50a and 50b, a transmission transistor (not shown), and a charge storage 55, an upper insulation layer 80 having a through-hole 85, and a photoelectric device 100.

However, unlike the above embodiment, in the CMOS image sensor 400 according to the present embodiment, the photo-sensing devices 50a and 50b are stacked in a vertical direction, but the color filter layer 70 is omitted. The photo-sensing devices 50a and 50b are electrically connected to charge storage (not shown) and may be transferred by the transmission transistor. The photo-sensing devices 50a and 50b may selectively absorb light in each wavelength region depending on a stacking depth.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

As described above, the photoelectric device selectively absorbing light in a green wavelength region is stacked and the red photo-sensing device and the blue photo-sensing device are stacked, and thereby a size of an image sensor may be reduced to realize a down-sized image sensor.

In FIG. 4, the photoelectric device selectively absorbing light in a green wavelength region is for example stacked, but this disclosure is not limited thereto. For example, a photoelectric device selectively absorbing light in a blue wavelength region may be stacked and a green photo-sensing device and a red photo-sensing device may be integrated in the semiconductor substrate 110 or a photoelectric device selectively absorbing light in a red wavelength region may be stacked and a green photo-sensing device and a blue photo-sensing device may be integrated in the semiconductor substrate 110.

Figure 5:
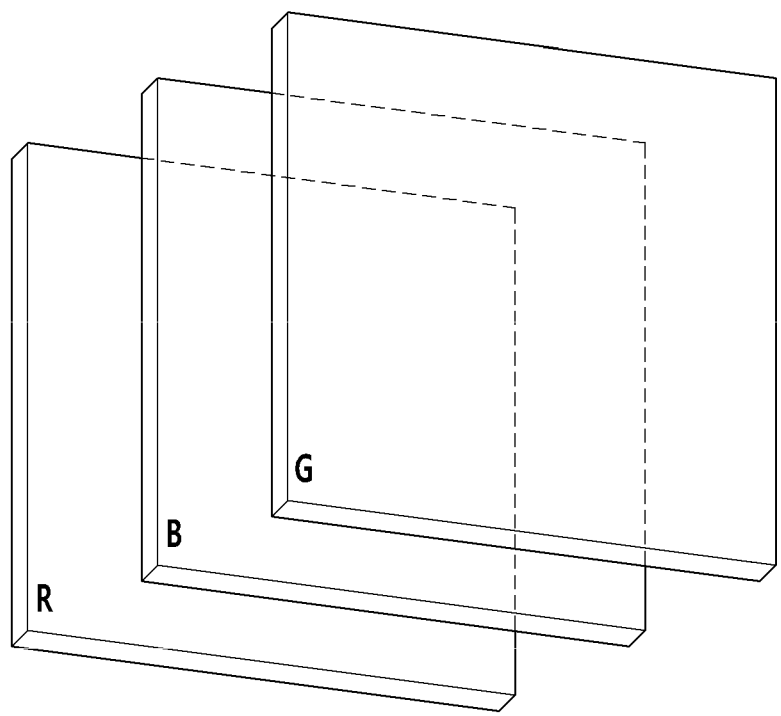
FIG. 5 is a schematic top plan view showing an organic CMOS image sensor according to another embodiment.
Figure 6:
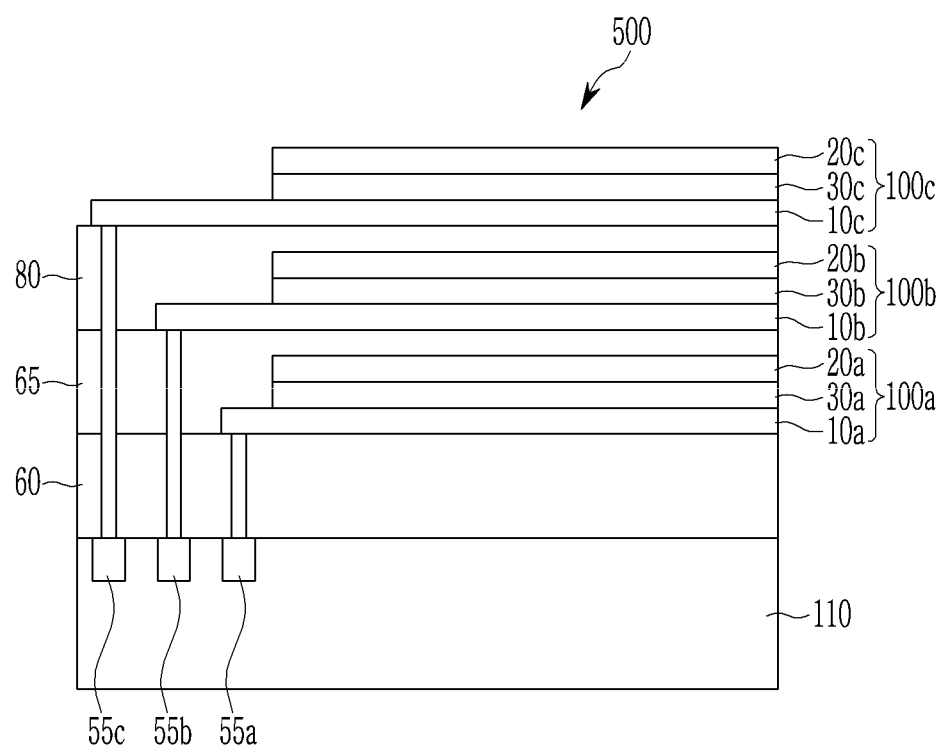
FIG. 6 is a cross-sectional view showing one example of the organic CMOS image sensor of FIG. 5.

FIG. 5 is a schematic top plan view showing an organic CMOS image sensor according to another embodiment and FIG. 6 is a cross-sectional view of the organic CMOS image sensor of FIG. 5.

The organic CMOS image sensor 500 according to the present embodiment includes a photoelectric device selectively absorbing light in a green wavelength region, a photoelectric device selectively absorbing light in a blue wavelength region, and a photoelectric device selectively absorbing light in a red wavelength region that are stacked.

The organic CMOS image sensor 500 according to the present embodiment includes a semiconductor substrate 110, a lower insulation layer 60, an intermediate insulation layer 65, an upper insulation layer 80, a first photoelectric device 100a, a second photoelectric device 100b, and a third photoelectric device 100c.

The semiconductor substrate 110 may be a silicon substrate, and is integrated with the transmission transistor (not shown) and the charge storages 55a, 55b, and 55c.

A metal line (not shown) and pad (not shown) are formed on the semiconductor substrate 110 and a lower insulation layer 60 is formed on the metal line and pad.

The first photoelectric device 100a is formed on the lower insulation layer 60.

The first photoelectric device 100a includes a first electrode 10a and a second electrode 20a facing each other and an organic layer 30a disposed between the first electrode 10a and the second electrode 20a. The first electrode 10a, the second electrode 20a, and the organic layer 30a are the same as described above and the organic layer 30a may selectively absorb light in one wavelength region of red, blue, and green. For example, the first photoelectric device 100a may be a red photoelectric device.

In the drawing, the first electrode 10a, the organic layer 30a, and the second electrode 20a are sequentially stacked, but this disclosure is not limited thereto, and for example they may be stacked in an order of the second electrode 20a, the organic layer 30a, and the first electrode 10a.

The intermediate insulation layer 65 is formed on the first photoelectric device 100a.

The second photoelectric device 100b is formed on the intermediate insulation layer 65.

The second photoelectric device 100b includes a first electrode 10b and a second electrode 20b facing each other and an organic layer 30b disposed between the first electrode 10b and the second electrode 20b. The first electrode 10b, the second electrode 20b, and the organic layer 30b are the same as described above and the organic layer 30b may selectively absorb light in one wavelength region of red, blue and green. For example, the second photoelectric device 100b may be a blue photoelectric device.

In the drawing, the first electrode 10b, the organic layer 30b, and the second electrode 20b are sequentially stacked, but this disclosure is not limited thereto, and for example they may be stacked in an order of the second electrode 20b, the organic layer 30b, and the first electrode 10b.

The upper insulation layer 80 is formed on the second photoelectric device 100b. The lower insulation layer 60, the intermediate insulation layer 65, and the upper insulation layer 80 have a plurality of through-holes exposing the charge storages 55a, 55b, and 55c.

The third photoelectric device 100c is formed on the upper insulation layer 80. The third photoelectric device 100c includes a first electrode 10c and a second electrode 20c facing each other and an organic layer 30c disposed between the first electrode 10c and the second electrode 20c. The first electrode 10c, the second electrode 20c, and the organic layer 30c are the same as described above and the organic layer 30c may selectively absorb light in one wavelength region of red, blue, and green. For example, the third photoelectric device 100c may be a green photoelectric device.

In the drawing, the first electrode 10c, the organic layer 30c, and the second electrode 20c are sequentially stacked, but this disclosure is not limited thereto, and for example they may be stacked in an order of the second electrode 20c, the organic layer 30c, and the first electrode 10c.

Focusing lens (not shown) may be further formed on the photoelectric device 100c. The focusing lens may control a direction of incident light and gather the light in one region. The focusing lens may have a shape of, for example, a cylinder or a hemisphere, but is not limited thereto.

In the drawing, the first photoelectric device 100a, the second photoelectric device 100b, and the third photoelectric device 100c are sequentially stacked, but the present disclosure is not limited thereto, and they may be stacked in various orders.

As described above, the first photoelectric device 100a, the second photoelectric device 100b, and the third photoelectric device 100c that absorb light in different wavelength regions are stacked, and thereby a size of an image sensor may be reduced to realize a down-sized image sensor.

The image sensor may be applied to, for example, various electronic devices such as a mobile phone or a digital camera, but is not limited thereto.

Hereinafter, the embodiments are illustrated in more detail with reference to examples. However, these examples are non-limiting, and the scope of claims is not limited thereto.

SYNTHESIS EXAMPLES

Synthesis Example 1

[Chemical Formula 1aa]

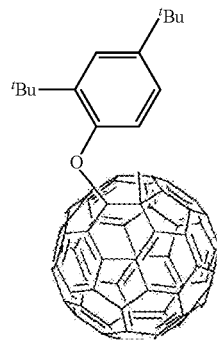

0.1 g of N-tosyl[1,2]aziridino[60]fullerene (C60NTs), 0.03 g of 1.5 equivalent-2,4-di-t-butylphenol (2,4-di-tert-butylphenol) are added to 11 ml of 1,2-dichlorobenzene (ODCB) under a nitrogen atmosphere, and the mixture is stirred at room temperature for 10 minutes. Subsequently, 1 µl of trifluoromethane sulfonic acid (TfOH) is added thereto, and the obtained mixture is stirred at 100° C. for 12 hours. The resultant is cooled down to room temperature and then, purified through silica gel column chromatography (a solvent: CS2) and concentrated. Then, the obtained product is dissolved in toluene, and a product therein is separated with recycled HPLC (a solvent: toluene, a column: Bucky prep) to obtain 0.05 g of a compound represented by Chemical Formula 1aa. A yield is 53%.

1H NMR (500 MHz, CS2/CDCl3=7/3): δ 7.71 (s, 1H), 7.45 (s, 1H), 1.70 (s, 9H), 1.35 (s, 9H).

Synthesis Example 2

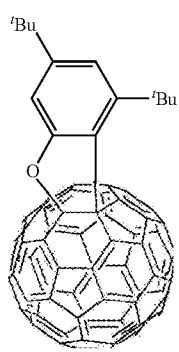

[Chemical Formula 1ab]

0.05 g of a compound represented by Chemical Formula 1ab is synthesized according to the same method as Synthesis Example 1 except for using 0.03 g of 3,5-di-t-butyl phenol instead of 0.03 g of 2,4-di-t-butylphenol. A yield is 55%.

1H NMR (500 MHz, CS2/CDCl3=7/3): δ 7.97 (s, 1H), 7.75 (s, 1H), 7.43-7.49 (m, 2H), 7.42 (d, 1H), 6.88 (d, 1H).

1H NMR (500 MHz, CS2/CDCl3=7/3): δ 7.38 (s, 1H), 6.88 (s, 1H), 1.70 (s, 9H), 1.35 (s, 9H).

Synthesis Example 3

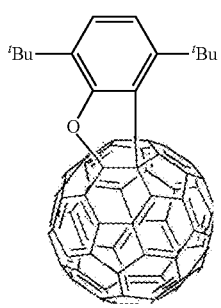

[Chemical Formula 1ac]

0.05 g of a compound represented by Chemical Formula 1ac is synthesized according to the same method as Synthesis Example 1 except for using 0.03 g of 2,5-di-t-butyl phenol instead of 0.03 g of 2,4-di-t-butylphenol. A yield is 57%.

1H NMR (500 MHz, CS2/CDCl3=7/3): δ 7.56 (d, 1H), 7.25 (d, 1H), 1.70 (s, 9H), 1.35 (s, 9H).

Synthesis Example 4

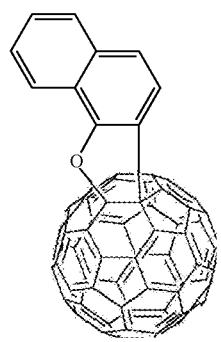

[Chemical Formula 1ad]

0.03 g of a compound represented by Chemical Formula 1ad is synthesized according to the same method as Synthesis Example 1 except for using 0.03 g of 1-naphthol instead of 0.03 g of 2,4-di-t-butylphenol. A yield is 30%.

1H NMR (500 MHz, CS2/CDCl3=7/3): δ 8.38 (d, 1H), 7.97 (d, 1H), 7.89 (d, 1H), 7.69 (d, 1H), 7.63 (dd, 2H).

Synthesis Example 5

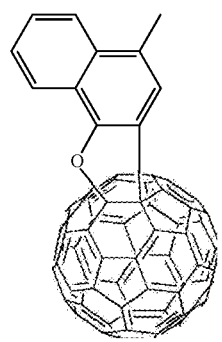

[Chemical Formula 1ae]

0.03 g of a compound represented by Chemical Formula 1ae is synthesized according to the same method as Synthesis Example 1 except for using 0.03 g of 4-methyl-1-naphthol instead of 0.03 g of 2,4-di-t-butylphenol. A yield is 30%.

1H NMR (500 MHz, CS2/CDCl3=7/3): δ 8.38 (d, 1H), 7.89 (s, 1H), 7.69 (d, 1H), 7.63 (dd, 2H), 2.55 (s, 3H).

Comparative Synthesis Example 1

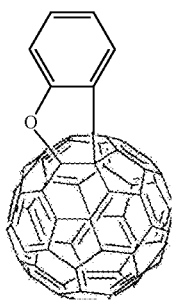

[Chemical Formula A]

0.03 g of a compound represented by Chemical Formula A is synthesized by using 0.20 g of chlorofullerene ($C_{60}Cl_6$) with a reference to a synthesis method of Org. Biomol. Chem., 2003, 1, 1764-1768 and J. Mater. Chem. A, 2017, 5, 2774-2783. A yield is 23%.

Data of $^1H$ NMR perfectly correspond with those which are described in Org. Biomol. Chem., 2003, 1, 1764-1768.

Comparative Synthesis Example 2

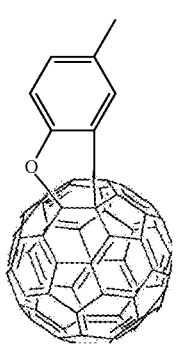

[Chemical Formula B]

0.05 g of a compound represented by Chemical Formula B is synthesized according to the same method as Synthesis Example 1 except for using 0.20 g of 4-methylphenol instead of 0.03 g of 2,4-di-t-butylphenol. A yield is 53%.

Data of 1H NMR perfectly correspond with those which are described in J. Mater. Chem. A, 2017, 5, 2774-2783.

Comparative Synthesis Example 3

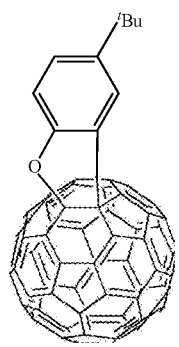

[Chemical Formula C]

0.05 g of a compound represented by Chemical Formula C is synthesized according to the same method as Synthesis Example 1 except for using 0.03 g of 4-t-butylphenol instead of 0.03 g of 2,4-di-t-butylphenol. A yield is 45%.

Data of 1H NMR perfectly correspond with those which are described in J. Am. Chem. Soc. 2011, 133, 2402-2405.

Comparative Synthesis Example 4

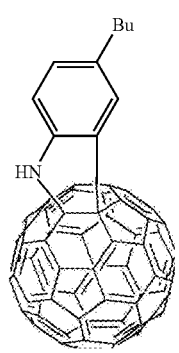

[Chemical Formula D]

0.03 g of a compound represented by Chemical Formula D is synthesized according to the same method as Synthesis Example 1 except for using 0.03 g of 4-butylaniline instead of 0.03 g of 2,4-di-t-butylphenol and stirring the mixture at 100° C. for 48 hours. A yield is 37%.

Data of 1H NMR perfectly correspond with those which are described in J. Am. Chem. Soc. 2011, 133, 2402-2405.

Comparative Synthesis Example 5

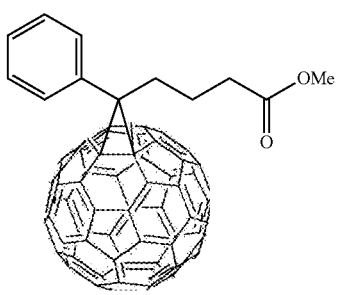
[Chemical Formula E]

A compound represented by Chemical Formula E (tradename: NANOM SPECTRA E102, Frontier Carbon Corporation) is purchased.

Comparative Synthesis Example 6

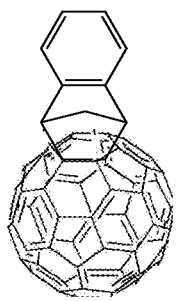
[Chemical Formula F]

A compound represented by Chemical Formula F (tradename: nanom spectra Q100, Frontier Carbon Corporation) is purchased.

Comparative Synthesis Example 7

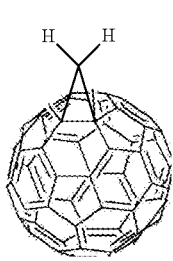
[Chemical Formula G]

0.2 g of a compound represented by Chemical Formula G is synthesized according to the same method as described in J. Am. Chem. Soc. 133, 8086 2011 by using 0.3 g of fullerene C60 under a nitrogen atmosphere. A yield after separation is 64%.

Data of 1H NMR perfectly correspond with those which are described in J. Am. Chem. Soc. 133, 8086 (2011).

Comparative Synthesis Example 8

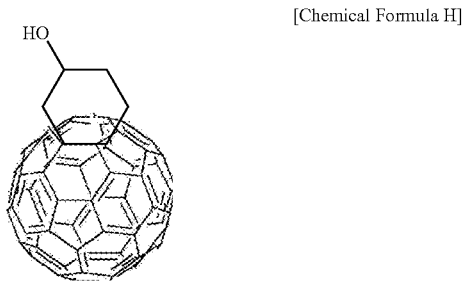
[Chemical Formula H]

0.2 g of a compound represented by Chemical Formula H is synthesized according to the same method as a method described in J. Org. Chem. 58, 4799 (1993) by using 0.3 g of fullerene C60 under a nitrogen atmosphere. A whole yield is 55%.

Data of 1H NMR perfectly correspond with those which are described in J. Org. Chem. 58, 4799 (1993).

Comparative Synthesis Example 9

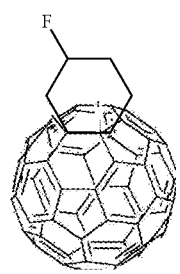
[Chemical Formula I]

0.2 g of a compound represented by Chemical Formula I is obtained by substituting a hydroxyl group in 0.2 g of the compound represented by Chemical Formula H with fluorine by using Deoxo-Fluor, a general deoxydation fluoridation reagent. A whole yield is 47%.

1H NMR (500 MHz, CS2/CDCl3=2/1): δ 2.7 (1H), 3.3 (1H), 3.4 (1H), 3.6 (1H), 3.7 (1H), 3.8 (1H), 5.2 (1H)

Reference Example (C60 Fullerene)

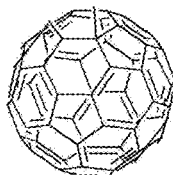
[Chemical Formula K]

A compound represented by Chemical Formula K (tradename: Nanom Purple ST, Frontier Carbon Corporation) is purchased.
Evaluation
Evaluation I
The fullerene derivatives according to Synthesis Examples 1 to 5 and Comparative Synthesis Examples 1 to 9, and fullerene according to Reference Example are respectively evaluated regarding a vacuum deposition through sublimation.

All organic materials are acquired using thermogravimetric analysis (TGA) under high vacuum (0.1-1.0 Pa). This equipment is called as the vacuum TGA. The sample (ca. 5 mg) is added to the platinum crucible, and set it to the equipment. Then the equipment is vacuumed to less than or equal to 1 Pa, for example 0.1 Pa. Analysis is started at room temperature, and reached to set temp. (Max temp. is 800° C.) at a rate of 10° C./min. The −10% weight loss and −50% weight loss are judged in this system. After analysis using vacuum TGA, referring to that temperature, set that in the sublimation equipment.

The evaluation is performed by increasing a temperature under high vacuum of less than or equal to a vacuum degree of 1 Pa to judge the sublimation or not, and herein, a compound having a 50% weight loss at a temperature of less than 500° C. (Ts) is judged to have a sublimable structure.

In Table 1, a sublimable compound is marked as "○," but a non-sublimable compound is marked as "×."

TABLE 1

| | Structure | $T_s$(°C) (−10 wt %) | $T_s$(°C) (−50 wt %) | Sublimable or not |
|---|---|---|---|---|
| Synthesis Example 1 | 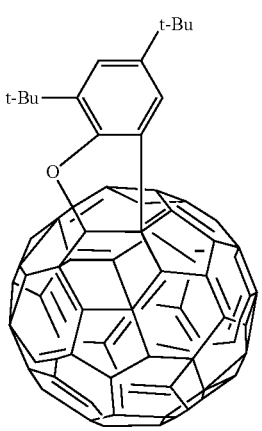 | 400 | 450 | ○ |
| Synthesis Example 2 | 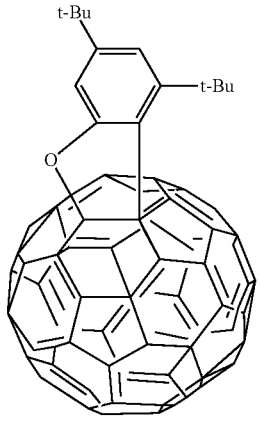 | 400 | 450 | ○ |
| Synthesis Example 3 | 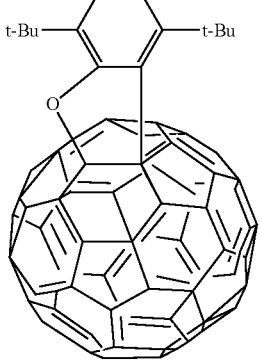 | 400 | 450 | ○ |

TABLE 1-continued
| | Structure | $T_s(°C)$ (−10 wt %) | $T_s(°C)$ (−50 wt %) | Sublimable or not |
|---|---|---|---|---|
| Synthesis Example 4 | 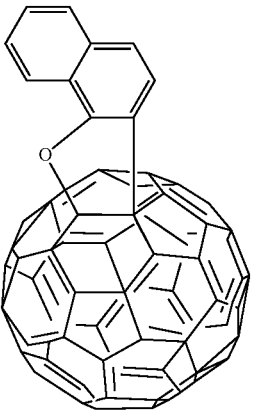 | 410 | 460 | ○ |
| Synthesis Example 5 | 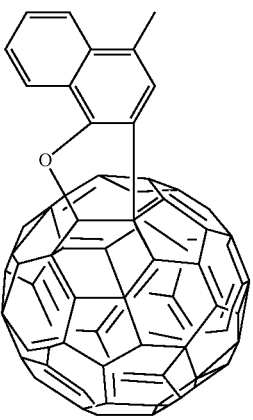 | 410 | 460 | ○ |
| Comparative Synthesis Example 1 | 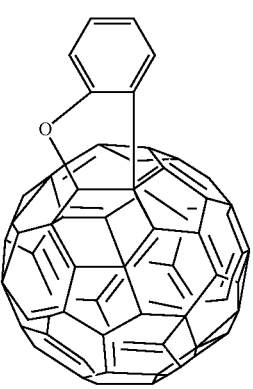 | 440 | 510 | X (C60 sublimation after decomposition of substituent) |

TABLE 1-continued
| | Structure | $T_s$(°C) (−10 wt %) | $T_s$(°C) (−50 wt %) | Sublimable or not |
|---|---|---|---|---|
| Comparative Synthesis Example 2 | 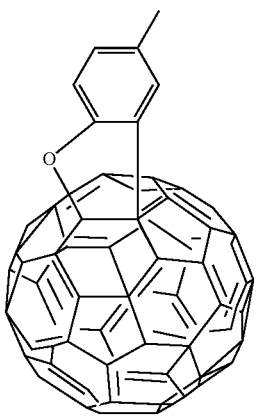 | 420 | — | X (polymerization) |
| Comparative Synthesis Example 3 | 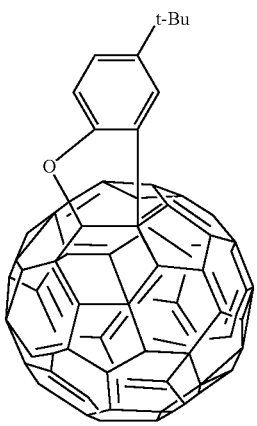 | 400 | 500 | X (polymerization) |
| Comparative Synthesis Example 4 | 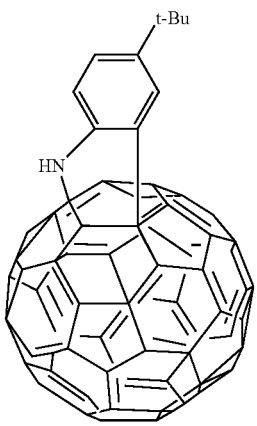 | 550 | — | X (polymerization) |

TABLE 1-continued
| | Structure | $T_s$(°C) (−10 wt %) | $T_s$(°C) (−50 wt %) | Sublimable or not |
|---|---|---|---|---|
| Comparative Synthesis Example 5 | 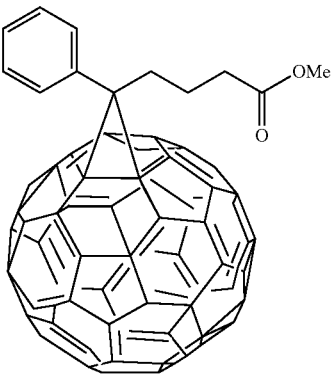 | 320 | 520 | X (C60 sublimation after decomposition of substituent) |
| Comparative Synthesis Example 6 | 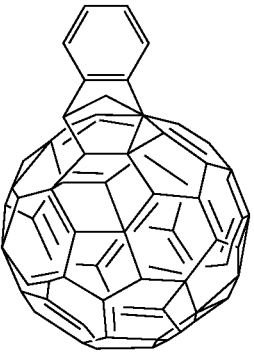 | 320 | 520 | X (C60 sublimation after decomposition of substituent) |
| Comparative Synthesis Example 7 | 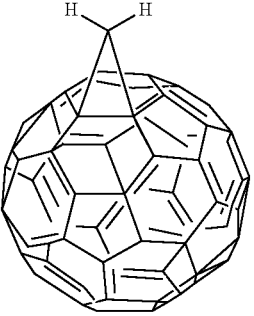 | 560 | — | X (polymerization) |
| Comparative Synthesis Example 8 | 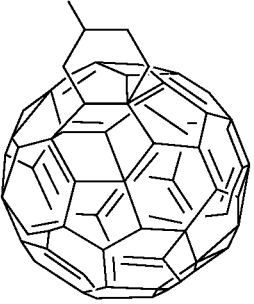 | 540 | — | X (polymerization) |

TABLE 1-continued

| | Structure | $T_s$(°C) (−10 wt %) | $T_s$(°C) (−50 wt %) | Sublimable or not |
|---|---|---|---|---|
| Comparative Synthesis Example 9 | F-fullerene structure | 550 | — | X (polymerization) |
| Reference Example (fullerene) | fullerene structure | 450 | 500 | O |

**$T_s$(°C) (−10 wt %): a temperature where a sample has a 10 wt % weight loss
*$T_s$(°C) (−50 wt %): a temperature where a sample has a 50 wt % weight loss Referring to Table 1, it is confirmed that the fullerene derivatives according to Synthesis Examples 1 to 5 and the fullerene according to Reference Example are depositable compounds through sublimation.

Evaluation II

The fullerene or fullerene derivatives according to Synthesis Examples and Reference Example are respectively deposited on a glass substrate to form thin films, and an energy level of each obtained thin film is measured. The thin films are fabricated via thermal evaporation under high vacuum at a rate of 0.1-1.0 Å/s on dried glass substrates that had been cleaned with isopropyl alcohol (IPA) and acetone in an ultrasonic cleaner.

A HOMO energy level of the thin film is measured by using a photoelectron spectrometer (AC-3, RIKEN KEIKI Co. Ltd.), an optical absorption edge of the thin film is referred to be an energy band gap, and a LUMO energy level is obtained by subtracting the HOMO energy level from the energy band gap.

The results are shown in Table 2.

TABLE 2

| | HOMO (eV) | LUMO (eV) |
|---|---|---|
| Synthesis Example 1 | 6.1 | 4.3 |
| Synthesis Example 2 | 6.1 | 4.3 |
| Synthesis Example 3 | 6.1 | 4.3 |
| Synthesis Example 4 | 6.1 | 4.3 |
| Synthesis Example 5 | 6.1 | 4.3 |
| Reference Example (fullerene) | 6.4 | 4.2 |

Whether or not the fullerene derivatives and the fullerene are desirable for an n-type semiconductor is examined by comparing the obtained energy levels with energy levels of a p-type semiconductor represented by Chemical Formula X and a p-type semiconductor represented by Chemical Formula Y.

[Chemical Formula X]

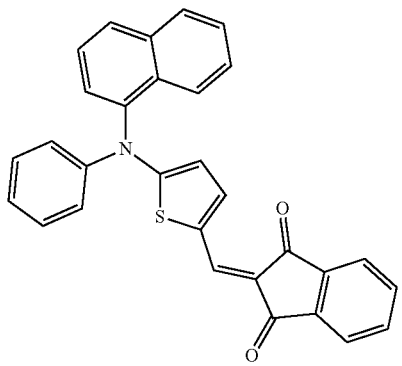

(HOMO energy level: 5.3 eV, LUMO energy level: 3.2 eV)

[Chemical Formula Y]

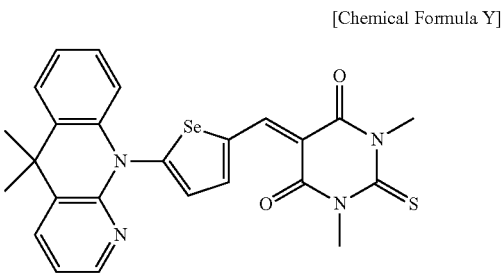

(HOMO energy level: 5.6 eV, LUMO energy level: 3.5 eV)

Accordingly, the fullerene derivatives according to Synthesis Examples 1 to 5 and the fullerene according to Reference Example have deeper HOMO and LUMO energy levels than those of the p-type semiconductor and thus may be used as an n-type semiconductor when the p-type semiconductor is used.

Evaluation III

Light absorption characteristics of each thin film formed by respectively depositing the fullerene or the fullerene derivative according to Synthesis Examples and Reference Example on a glass substrate are evaluated. The thin films are fabricated via thermal evaporation under high vacuum at a rate of 0.1-1.0 Å/s on dried glass substrates that had been cleaned with isopropyl alcohol (IPA) and acetone in an ultrasonic cleaner.

The light absorption characteristics of the thin films are evaluated by measuring light absorbance of a wavelength in an ultraviolet visible-near-infrared light region by using a UV-Vis spectrophotometer (Varian Cary 500 Bio spectrophotometer).

Figure 7:
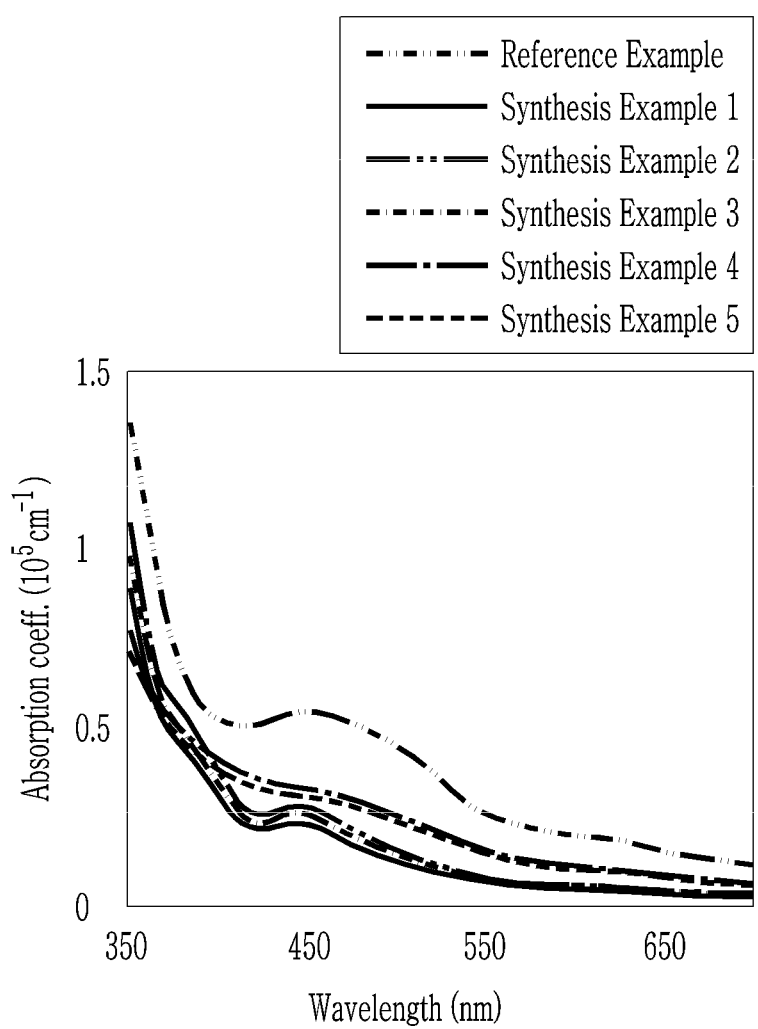
FIG. 7 is a graph showing light absorption characteristics of the fullerene derivatives according to Synthesis Examples 1 to 5 and fullerene according to Reference Example.

The results are shown in Table 3 and FIG. 7.

FIG. 7 is a graph showing light absorption characteristics of the fullerene or fullerene derivatives according to Synthesis Examples 1 and 2 and Reference Example.

TABLE 3

| | Abs. coeff. at 450 nm ($10^5$ cm$^{-1}$) |
|---|---|
| Synthesis Example 1 | 0.24 |
| Synthesis Example 2 | 0.28 |
| Synthesis Example 3 | 0.26 |
| Synthesis Example 4 | 0.34 |
| Synthesis Example 5 | 0.32 |
| Comparative Synthesis Example 1 | 0.42 (C60 sublimation after decomposition of substituent) |
| Reference Example (fullerene) | 0.55 |

Referring Table 3 and FIG. 7, the thin films respectively including the fullerene derivatives according to Synthesis Examples 1 to 5 show low extinction coefficient at about 450 nm (blue wavelength region) compared with the thin film including the fullerene according to Reference Example. From the results, the fullerene derivatives according to Synthesis Examples 1 to 5 show no abnormal light absorption characteristics in a short wavelength of a visible ray due to aggregation.

While this disclosure has been described in connection with what is presently considered to be practical example embodiments, it is to be understood that inventive concepts not limited to the disclosed embodiments, but, on the contrary, are intended to cover various modifications and equivalent arrangements included within the spirit and scope of the appended claims.

What is claimed is:

1. A fullerene derivative comprising:
a substituent represented by one of Chemical Formulae 3 to 8,

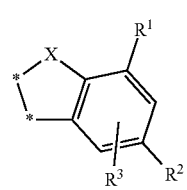

[Chemical Formula 3]

-continued

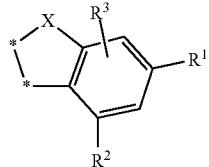

[Chemical Formula 4]

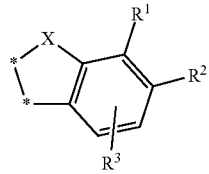

[Chemical Formula 5]

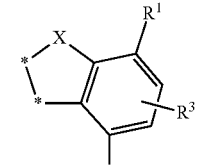

[Chemical Formula 6]

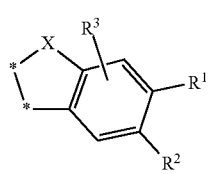

[Chemical Formula 7]

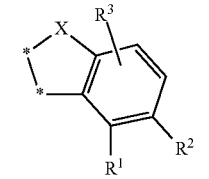

[Chemical Formula 8]

wherein, in Chemical Formulae 3 to 8,

X is one of O, S, Se, Te, SO, SO$_2$, CR$^b$R$^c$, SiR$^d$R$^e$, or GeR$^f$R$^g$, R$^1$ and R$^2$ are independently a substituted or unsubstituted C3 to C20 branched alkyl group, and R$^3$ and R$^b$ to R$^g$ are independently one of hydrogen, deuterium, a substituted or unsubstituted C1 to C20 alkyl group, a substitute or unsubstituted C1 to C20 heteroalkyl group, a substituted or unsubstituted C2 to C20 alkenyl group, a substituted or unsubstituted C2 to C20 heteroalkenyl group, a substituted or unsubstituted C6 to C30 aryl group, a substituted or unsubstituted C3 to C30 heterocyclic group, a halogen, a cyano group, or a combination thereof, and

* is a linking point with a fullerene core.

2. The fullerene derivative of claim 1, wherein the fullerene derivative is a vacuum-depositable compound by sublimation.

3. The fullerene derivative of claim 2, wherein
the fullerene derivative exhibits 10% weight loss relative to an initial weight at a temperature of less than or equal to about 450° C., and
the fullerene derivative exhibits 50% weight loss relative to the initial weight at a temperature of less than or equal to about 500° C.

4. The fullerene derivative of claim 1, wherein
the fullerene derivative has a LUMO energy level of about 3.7 eV to about 5.0 eV, and the fullerene derivative has a HOMO energy level of about 5.8 eV to about 7.0 eV.

5. The fullerene derivative of claim 1, wherein the fullerene core is one of C60, C70, C74, C76, or C78.

6. The fullerene derivative of claim 1, wherein $R^1$ and $R^2$ are independently one of an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

7. The fullerene derivative of claim 1, wherein the substituent is represented by one of Chemical Formulae 1A to 1C:

[Chemical Formula 1A]

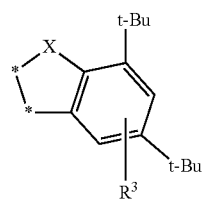

[Chemical Formula 1B]

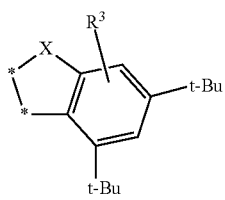

[Chemical Formula 1C]

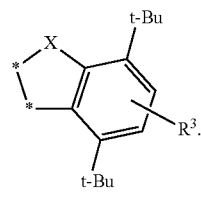

8. A thin film comprising:
the fullerene derivative of claim 1.

9. The thin film of claim 8, wherein an extinction coefficient at a a wavelength of 450 nm of the thin film is smaller than an extinction coefficient at a wavelength of 450 nm of a thin film including unsubstituted C60 fullerene.

10. The thin film of claim 9, wherein the extinction coefficient at a wavelength of 450 nm of the thin film is less than or equal to about ½ of the extinction coefficient at a wavelength of 450 nm of a thin film including unsubstituted C60 fullerene.

11. A photoelectric device comprising
a first electrode and a second electrode facing each other; and
an organic layer disposed between the first electrode and the second electrode,
wherein the organic layer includes a fullerene derivative having a substituent represented by one of Chemical Formulae 3 to 8,

[Chemical Formula 3]

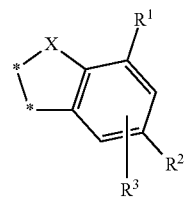

[Chemical Formula 4]

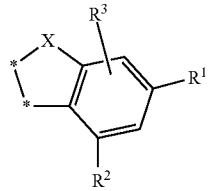

[Chemical Formula 5]

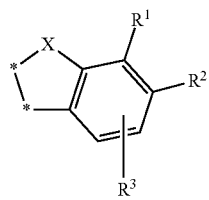

[Chemical Formula 6]

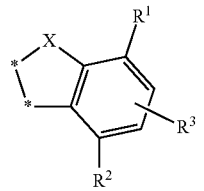

[Chemical Formula 7]

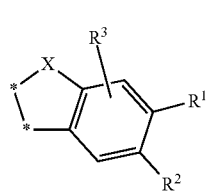

[Chemical Formula 8]

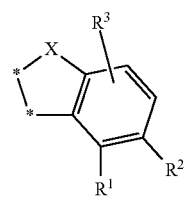

wherein, in Chemical Formulae 3 to 8,

X is one of O, S, Se, Te, SO, $SO_2$, $CR^bR^c$, $SiR^dR^e$, or $GeR^fR^g$, $R^1$ and $R^2$ are independently a substituted or unsubstituted C3 to C20 branched alkyl group, and $R^3$ and $R^b$ to $R^g$ are independently one of hydrogen, deuterium, a substituted or unsubstituted C1 to C20 alkyl group, a substitute or unsubstituted C1 to C20 heteroalkyl group, a substituted or unsubstituted C2 to C20 alkenyl group, a substituted or unsubstituted C2 to C20 heteroalkenyl group, a substituted or unsubstituted C6 to C30 aryl group, a substituted or unsubstituted C3 to C30 heterocyclic group, a halogen, a cyano group, or a combination thereof, and

* is a linking point with a fullerene core.

12. The photoelectric device of claim 11, wherein the fullerene core is one of C60, C70, C74, C76, or C78.

13. The photoelectric device of claim 11, wherein $R^1$ and $R^2$ are one of an isopropyl group, an isobutyl group, an isopentyl group, an isohexyl group, an isoheptyl group, an isooctyl group, a t-butyl group, a t-pentyl group, a t-hexyl group, a neopentyl group, or a neohexyl group.

14. The photoelectric device of claim 11, wherein the substituent is represented by one of Chemical Formulae 1A to 1C:

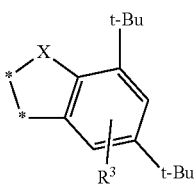

[Chemical Formula 1A]

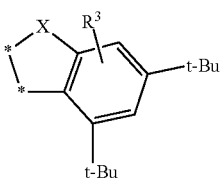

[Chemical Formula 1B]

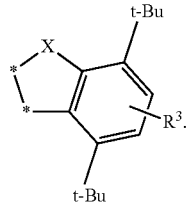

[Chemical Formula 1C]

15. The photoelectric device of claim 11, wherein
the organic layer includes an active layer,
the active layer includes a p-type semiconductor and an n-type semiconductor that form a pn junction, and
the n-type semiconductor includes the fullerene derivative.

16. An image sensor comprising:
the photoelectric device of claim 11.

17. An electronic device comprising:
the image sensor of claim 16.

18. An electronic device comprising:
the photoelectric device of claim 11.

* * * * *